(12) United States Patent
Pasquier et al.

(10) Patent No.: US 7,658,770 B2
(45) Date of Patent: *Feb. 9, 2010

(54) AGENTS FOR COLORING KERATIN FIBERS

(75) Inventors: Cécile Pasquier, Marly (CH); Eric Tinguely, Fribourg (CH); Markus Speckbacher, Aschaffenburg (DE); Annik Marguet, Villarsel-Le-Gibloux (CH); Hans-Jürgen Braun, Ueberstorf (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/393,505

(22) Filed: Feb. 26, 2009

(65) Prior Publication Data

US 2009/0165221 A1     Jul. 2, 2009

Related U.S. Application Data

(63) Continuation of application No. 11/707,310, filed on Feb. 16, 2007, now Pat. No. 7,513,916.

(30) Foreign Application Priority Data

Feb. 18, 2006     (EP) ................... 06003344

(51) Int. Cl.
*A61Q 5/10*     (2006.01)
*C09B 44/10*    (2006.01)

(52) U.S. Cl. ............ 8/405; 8/407; 8/435; 8/455; 8/466; 8/568; 8/570; 8/571; 8/572; 8/573; 8/575; 8/576; 534/606

(58) Field of Classification Search ............ 8/405, 8/407, 435, 455, 466, 568, 570, 571, 572, 8/573, 575, 576; 534/606
See application file for complete search history.

(56) References Cited

U.S. PATENT DOCUMENTS

| 3,578,386 | A |   | 5/1971 | Kalopissis et al. |
| 4,432,899 | A |   | 2/1984 | Linhart et al. |
| 5,284,939 | A | * | 2/1994 | Nicopoulos et al. ......... 534/582 |
| 7,513,916 | B2 | * | 4/2009 | Pasquier et al. ............. 8/405 |

FOREIGN PATENT DOCUMENTS

| DE | 19618595 A1 | 11/1997 |
| DE | 10118271 A1 | 3/2002 |
| FR | 2782035 A1 | 2/2000 |
| GB | 1147546 A | 4/1969 |
| GB | 1162665 A | 8/1969 |
| GB | 1183620 A | 3/1970 |
| GB | 1493380 A | 11/1977 |
| WO | WO-95/01722 A1 | 1/1995 |
| WO | WO-97/20545 A1 | 6/1997 |

OTHER PUBLICATIONS

International Search Report for PCT/US2007/003554, Jul. 4, 2007 (6 pages).
Xie, Kongliang et al., "Synthesis of Reactive-Cation Dyes with Pyridinium Acetamide," XP002388786, Retrieved from STN Database Accession No. 1992:552674 (Abstract).

* cited by examiner

*Primary Examiner*—Eisa B Elhilo
(74) *Attorney, Agent, or Firm*—Melissa G. Krasovec

(57) ABSTRACT

The present invention relates to agents for coloring keratin fibers which comprise at least one cationic azodye of the general formula (I).

$$Y \overset{N}{\underset{Z}{\diagdown}} \underset{X}{\diagup} - N = N - \underset{}{\bigcirc} - \underset{R2}{\overset{}{\bigcirc}} - \underset{}{\overset{R1}{\underset{}{N}}} - (\phantom{x})_n - Q^+ \, An^-$$

(I)

10 Claims, No Drawings

AGENTS FOR COLORING KERATIN FIBERS

CROSS REFERENCE TO RELATED APPLICATIONS

This application is continuation of U.S. application Ser. No. 11/707,310 filed on Feb. 16, 2007 now U.S. Pat. No. 7,513,916.

FIELD OF THE INVENTION

The present invention relates to agents for coloring keratin fibers, such as, for example, wool, furs and, in particular, human hair, comprising cationic azodyes.

BACKGROUND OF THE INVENTION

For the color-changing treatment of keratin fibers two coloring methods usually are used. In the first method, the coloration is produced with so-called oxidative or permanent colorants using a mixture of various developer substances and coupler substances and an oxidizing agent. If required, in this method, so-called direct (nonoxidative) dyes can be added to top off the coloring result or to produce particular color effects. The second method uses exclusively direct dyes, which are applied to the fibers in a suitable carrier mass. This method is easy to use, exceptionally gentle and is characterized by low damage to keratin fibers. The direct dyes used here are subject to a large number of requirements. For example, they have to be acceptable from a toxicological and dermatological point of view and allow the attainment of colorations in the desired intensity, which, inter alia, also requires adequate solubility in water. In addition, good lightfastness, acid fastness, and rubbing fastness is required for the colorations achieved.

Compared with oxidative colorations, nonoxidative colorations, however, generally have lower durability and a poorer eveness of color. In addition, direct colorants are generally not able to "lighten" the hair since many direct dyes do not withstand the oxidizing agents required for the lightening and/or the required pH of greater than or equal to 9.

WIPO Application No. WO 95/01722 A1 and WO 97/20545 A1 disclose colorants which comprise cationic azo dyes, in which the positive charge is delocalized in the conjugated system. Cationic azodyes, in which the cationic charge is localized in a side chain, are known to dye synthetic fibres, as described in European Patent No. EP 56578 A1, for example. German Patent No. DE 10118271 A1 discloses among others cationic disazodiazole derivatives and their use in hair dyes.

SUMMARY OF THE INVENTION

It has now been found that special cationic azodyes color can dye keratin fibers intensely and durably, are oxidation-stable, and thus can also be used in oxidative coloring systems.

DETAILED DESCRIPTION OF THE INVENTION

The present invention therefore provides:
(a) an agent for the nonoxidative coloring of keratin fibers, in particular human hair;
(b) an agent for the simultaneous lightening and coloring of keratin fibers, in particular human hair, which, besides the dye of the formula (I), comprises an oxidizing agent; and
(c) an oxidative colorant for keratin fibers, in particular human hair, based on at least one oxidation dye precursor;

where the agents (a), (b), and (c) are characterized by comprising at least one azodye of the general formula (I);

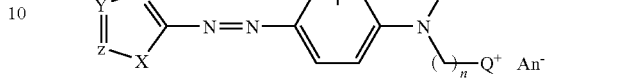

in which
X is oxygen, sulfur, N—R3, C—R4;
Y is C—R5, nitrogen, N—R6, sulfur or oxygen;
Z is C—R7 or nitrogen;
with the proviso that the heterocycle of the formula (I) comprises at least two and at most three heteroatoms, where the heterocycle has at most one sulfur atom or one oxygen atom;
n is an integer from 1 to 6;
R1 is hydrogen, a saturated or unsaturated $(C_1-C_{12})$-alkyl group, a $(C_1-C_{12})$-alkyl group substituted by a halogen atom (F, Cl, Br, I), a hydroxy-$(C_2-C_{12})$-alkyl group, an amino-$(C_1-C_{12})$-alkyl group, a substituted or unsubstituted phenyl group or a substituted or unsubstituted benzyl group;
R2, R4, R5, and R7 may be identical or different and, independently of one another, are hydrogen, a halogen atom (F, Cl, Br, I), a saturated or unsaturated $(C_1-C_2)$-alkyl group, a $(C_1-C_{12})$-alkyl group substituted by a halogen atom (F, Cl, Br, I), a hydroxyl group, a hydroxy-$(C_1-C_{12})$-alkyl group, a $(C_1-C_{12})$-alkoxy group, a $(C_1-C_{12})$-thioalkyl group, a cyano group, a nitro group, an amino group, a $(C_1-C_{12})$-alkylamino group, a $(C_1-C_2)$-dialkylamino group, a carboxylic acid group, a $C(O)O—(C_1-C_{12})$-alkyl group, a substituted or unsubstituted $C(O)O$-phenyl group, a substituted or unsubstituted phenyl group or a naphthyl group, a substituted or unsubstituted heteroaryl group;
or if Y and Z are C—R5 and C—R7, the radical groups R5 and R7, together with the remaining molecule, can form a heterocyclic or carbocyclic, saturated or unsaturated, substituted or unsubstituted ring system;
or if X and Y are C—R4 and C—R5, the radical groups R4 and R5, together with the remaining molecule, can form a heterocyclic or carbocyclic, saturated or unsaturated, substituted or unsubstituted ring system;
R3 and R6 may be identical or different and, independent of one another, are a saturated or unsaturated $(C_1-C_{12})$-alkyl group, a $(C_1-C_{12})$-alkyl group substituted by a halogen atom (F, Cl, Br, I), a hydroxy-$(C_2-C_{12})$-alkyl group, an amino-$(C_1-C_{12})$-alkyl group, a substituted or unsubstituted phenyl group or a substituted or unsubstituted benzyl group;
Q+ represents an aromatic or non aromatic, substituted or unsubstituted 4- to 6-membered heterocyclic quaternary ammonium group, which may contain other heteroatoms like nitrogen, sulfur, or oxygen, with the proviso that the cationic heterocycle comprises at most three heteroatoms, where the heterocycle has at most one sulfur atom or oxygen atom;
or the radical group R1, together with Q+, can form a 5 or 6-membered unsaturated heterocyclic, substituted or unsubstituted cationic ring system;

the anion An- is an organic or inorganic acid anion, such as, for example, halogen anions (chloride, bromide, iodide), sulfate, acetate, formate, propionate, lactate, perchlorate, hexafluorophosphate, tetrafluoroborate, or tetraphenylborate.

Among the abovementioned compounds of the formula (I), preference is given to those in which Q+ represents a 5- to 6-membered aromatic or non-aromatic heterocyclic quaternary ammonium group of the formula (IIa to IIg)

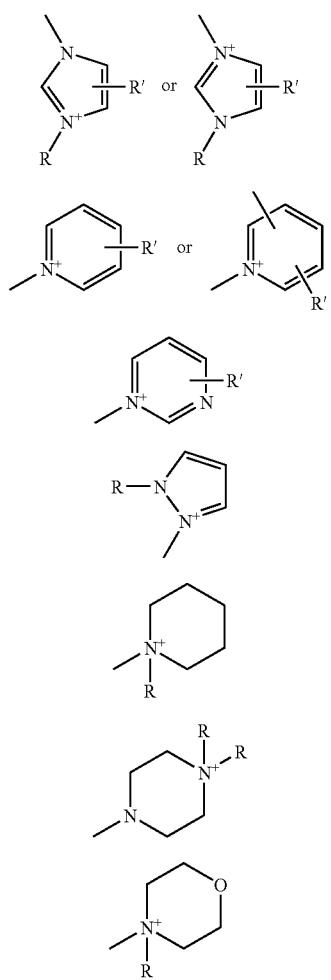

in which R is a saturated or unsaturated $(C_1-C_{12})$-alkyl group, R' may be hydrogen, a halogen atom (F, Cl, Br, I), a saturated or unsaturated $(C_1-C_{12})$-alkyl group, a $(C_1-C_{12})$-alkyl group substituted by a halogen atom (F, Cl, Br, I), a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a C(O)O—$(C_1-C_{12})$-alkyl group, a substituted or unsubstituted C(O)O-phenyl group, a substituted or unsubstituted phenyl group or a naphthyl group, a substituted or unsubstituted heteroaryl group.

Particularly preferred compounds of the general formula (I) are:
1-[2-(ethyl{4-[1,3-thiazol-2-yldiazenyl]phenyl}amino) ethyl]-3-methyl-1H-imidazol-3-ium bromide; 3-methyl-1-[2-(methyl{4-[1,3-thiazol-2-yldiazenyl]phenyl}amino) ethyl]-1H-imidazol-3-ium bromide; 1-[2-((2-hydroxyethyl) {4-[1,3-thiazol-2-yldiazenyl] phenyl}amino)ethyl]-3-methyl-1H-imidazol-3-ium bromide; 1-[2-(ethyl{3-methyl-4-[1,3-thiazol-2-yldiazenyl]phenyl}amino)ethyl]-3-methyl-1H-imidazol-3-ium bromide; 1-{2-[{3-chloro-4-[1,3-thiazol-2-yldiazenyl] phenyl}(ethyl)amino]ethyl}-3-methyl-1H-imidazol-3-ium bromide; 1-[2-(ethyl{4-[(4-methyl-1,3-thiazol-2-yl) diazenyl]phenyl}amino)ethyl]-3-methyl-1H-imidazol-3-ium bromide; 1-[2-(ethyl{3-methyl-4-[(4-methyl-1,3-thiazol-2-yl)diazenyl]phenyl}amino)-ethyl]-3-methyl-1H-imidazol-3-ium bromide; 1-{2-[{3-chloro-4-[(4-methyl-1,3-thiazol-2-yl)diazenyl]phenyl}(ethyl)amino] ethyl}-3-methyl-1H-imidazol-3-ium bromide; 1-[2-(ethyl{4-[(5-methyl-1,3-thiazol-2-yl)diazenyl]-phenyl}amino)ethyl]-3-methyl-1H-imidazol-3-ium bromide; 1-[2-(ethyl{3-methyl-4-[(5-methyl-1,3-thiazol-2-yl)diazenyl]phenyl}amino)-ethyl]-3-methyl-1H-imidazol-3-ium bromide; 1-{2-[{3-chloro-4-[(5-methyl-1,3-thiazol-2-yl)diazenyl]phenyl}(ethyl)amino]ethyl}-3-methyl-1H-imidazol-3-ium bromide; 1-{2-[{4-[(4,5-dimethyl-1,3-thiazol-2-yl)diazenyl]-phenyl}(ethyl) amino]ethyl}-3-methyl-1H-imidazol-3-ium bromide; 1-{2-[{4-[(4,5-dimethyl-1,3-thiazol-2-yl)diazenyl]-3-methylphenyl}(ethyl)-amino]ethyl}-3-methyl-1H-imidazol-3-ium bromide; 1-{2-[{3-chloro-4-[(4,5-dimethyl-1,3-thiazol-2-yl)diazenyl]phenyl}(ethyl)amino]ethyl}-3-methyl-1H-imidazol-3-ium bromide; 1-[2-(ethyl{4-[(5-nitro-1,3-thiazol-2-yl)diazenyl]phenyl}amino)ethyl]-3-methyl-1H-imidazol-3-ium bromide; 1-{2-[{4-[(4-chloro-5-nitro-1,3-thiazol-2-yl)diazenyl]phenyl}(ethyl)-amino] ethyl}-3-methyl-1H-imidazol-3-ium bromide; 1-[2-(ethyl{4-[(4-phenyl-1,3-thiazol-2-yl)diazenyl] phenyl}amino)ethyl]-3-methyl-1H-imidazol-3-ium bromide; 1-{2-[{4-[1,3-benzothiazol-2-yldiazenyl]-phenyl}(ethyl)amino]ethyl}-3-methyl-1H-imidazol-3-ium bromide; 1-[2-(ethyl{4-[(6-nitro-1,3-benzothiazol-2-yl) diazenyl]phenyl}amino)ethyl]-3-methyl-1H-imidazol-3-ium bromide; 1-[2-(ethyl{4-[(4,6-dinitro-1,3-benzothiazol-2-yl)diazenyl]phenyl}-amino)ethyl]-3-methyl-1H-imidazol-3-ium bromide; 1-[2-(ethyl{4-[(5,6-dinitro-1,3-benzothiazol-2-yl)diazenyl]-phenyl}amino)ethyl]-3-methyl-1H-imidazol-3-ium bromide; 1-[2-(ethyl{4-[1H-[1,3]thiazolo[5,4-f]indazol-6-yldiazenyl]phenyl}amino) ethyl]-3-methyl-1H-imidazol-3-ium bromide; 1-{2-[{4-[(5-chloro[1,3]thiazolo[5,4-b]pyridin-2-yl)diazenyl] phenyl}(ethyl)amino]ethyl}-3-methyl-1H-imidazol-3-ium bromide; 1-{2-[ethyl(4-{[5-(methoxy)[1,3]thiazolo [5,4-b]pyridin-2-yl]diazenyl}phenyl)amino]ethyl}-3-methyl-1H-imidazol-3-ium bromide; 1-[2-(ethyl{4-[1,3-thiazol-2-yldiazenyl]phenyl}amino)ethyl]-2,3-dimethyl-1H-imidazol-3-ium bromide; 1-[2-(ethyl{4-[(4-methyl-1,3-thiazol-2-yl)diazenyl]phenyl}amino)ethyl]-2,3-dimethyl-1H-imidazol-3-ium bromide; 1-[2-(ethyl{4-[(5-methyl-1,3-thiazol-2-yl)diazenyl]phenyl}amino)ethyl]-2,3-dimethyl-1H-imidazol-3-ium bromide; 1-{2-[{4-[(4,5-dimethyl-1,3-thiazol-2-yl)diazenyl]phenyl}-(ethyl) amino]ethyl}-2,3-dimethyl-1H-imidazol-3-ium bromide; 1-[3-(ethyl{4-[1,3-thiazol-2-yldiazenyl]phenyl}amino) propyl]-3-methyl-1H-imidazol-3-ium bromide; 1-[2-(ethyl{4-[1,3-thiazol-2-yldiazenyl]phenyl}amino)ethyl] pyridinium bromide; 1-[2-(ethyl{4-[(5-methyl-1,3-thiazol-2-yl)diazenyl]-phenyl}amino)ethyl]pyridinium bromide; 1-[2-(ethyl{4-[(4-methyl-1,3-thiazol-2-yl)diazenyl]phenyl}amino)ethyl]-pyridinium bromide; 1-{2-[{4-[(4,5-dimethyl-1,3-thiazol-2-yl)diazenyl]phenyl}-(ethyl)

amino]-ethyl}pyridinium bromide; 1-[2-(ethyl{3-methyl-4-[1,3-thiazol-2-yldiazenyl]-phenyl}amino)ethyl] pyridinium bromide; 1-{2-[{3-chloro-4-[1,3-thiazol-2-yldiazenyl]phenyl}(ethyl)amino]ethyl}pyridinium bromide; 1-[2-(ethyl{4-[(5-nitro-1,3-thiazol-2-yl)diazenyl]phenyl}amino)ethyl]pyridinium bromide; 1-[2-(ethyl{3-methyl-4-[(5-nitro-1,3-thiazol-2-yl)diazenyl]phenyl}amino)-ethyl]pyridinium bromide; 1-{2-[{3-(dimethylamino)-4-[1,3-thiazol-2-yldiazenyl]phenyl}(ethyl)amino]ethyl}-pyridinium bromide; 1-{2-[{3-(dimethylamino)-4-[(5-nitro-1,3-thiazol-2-yl)diazenyl]-phenyl}(ethyl)amino]-ethyl}pyridinium bromide; 4-[2-(ethyl{4-[1,3-thiazol-2-yldiazenyl]phenyl}amino)ethyl]-4-methylmorpholin-4-ium bromide; 4-{2-[{4-[1,3-benzothiazol-2-yldiazenyl]phenyl}-(ethyl)amino]ethyl}-4-methylmorpholin-4-ium bromide; 1-[2-(ethyl{4-[1,3-thiazol-2-yldiazenyl]-phenyl}amino)ethyl]-1-methylpiperidinium bromide; 4-[2-(ethyl{4-[1,3-thiazol-2-yldiazenyl]phenyl}amino)ethyl]-1,1-dimethylpiperazin-1-ium bromide; 1-[2-(ethyl{4-[1,3,4-thiadiazol-2-yldiazenyl]phenyl}amino)ethyl]-3-methyl-1H-imidazol-3-ium bromide; 1-[2-(ethyl{4-[(5-phenyl-1,3,4-thiadiazol-2-yl)diazenyl]phenyl}amino)ethyl]-3-methyl-1H-imidazol-3-ium bromide; 1-[2-(ethyl{4-[1,3,4-thiadiazol-2-yldiazenyl]phenyl}amino)-ethyl] pyridinium bromide; 1-[2-(ethyl{4-[(5-phenyl-1,3,4-thiadiazol-2-yl)diazenyl]phenyl}amino)ethyl]-pyridinium bromide; 1-[2-(ethyl{4-[1,2,4-thiadiazol-2-yldiazenyl]phenyl}amino)ethyl]-3-methyl-1H-imidazol-3-ium bromide; 1-[2-(ethyl{4-[(3-phenyl-1,2,4-thiadiazol-5-yl)diazenyl]-phenyl}amino)ethyl]-3-methyl-1H-imidazol-3-ium bromide; 1-{2-[{4-[(3-chloro-1,2,4-thiadiazol-5-yl)diazenyl]phenyl}(ethyl)amino]-ethyl}-3-methyl-1H-imidazol-3-ium bromide; 1-[2-(ethyl{4-[1,2,4-thiadiazol-5-yldiazenyl]phenyl}amino)ethyl] pyridinium bromide; 1-[2-(ethyl{4-[(3-phenyl-1,2,4-thiadiazol-5-yl)diazenyl]phenyl}amino)ethyl]pyridinium bromide; 2-(ethyl{4-[1H-1,2,4-triazol-5-yldiazenyl]-phenyl}amino)-3-methyl-1H-imidazol-3-ium bromide; 1-[2-(ethyl{4-[(1-methyl-1H-imidazol-2-yl)diazenyl]-phenyl}amino)ethyl]-3-methyl-1H-imidazol-3-ium bromide; 1-[2-(ethyl{3-methyl-4-[(1-methyl-1H-imidazol-2-yl)diazenyl]phenyl}amino)ethyl]-3-methyl-1H-imidazol-3-ium bromide; 1-{2-[{3-chloro-4-[(1-methyl-1H-imidazol-2-yl)diazenyl]phenyl}-(ethyl)amino]ethyl}-3-methyl-1H-imidazol-3-ium bromide.

The dyes of the formula (I) are present in the colorant according to the invention preferably in an amount of from 0.01% to 10% by weight, in particular from 0.1% to 8% by weight.

To extend the color pallet, the colorant (a) according to the invention can in addition to the dyes of the formula (I), also comprises further known direct synthetic dyes from the group consisting of nitro dyes, azo dyes, anthraquinone dyes, triphenylmethane dyes and basic or acidic dyes, and natural direct dyes, alone or in a mixture with one another.

The colorant (b) according to the invention, which comprises an oxidizing agent, preferably hydrogen peroxide, may, in addition to the dyes of the general formula (I), also comprise further oxidation-stable direct dyes, such as, for example, 3-(2',6'-diaminopyridyl-3'-azo)pyridine (=2,6-diamino-3-((pyridin-3-yl)azo)pyridine), N,N-di(2-hydroxyethyl)-3-methyl-4-((4-nitrophenyl)azo)aniline (Disperse Red 17, CI11210), 3-diethylamino-7-(4-dimethylaminophenylazo)-5-phenylphenazinium chloride (Cl11050), 4-(2-thiazolylazo)-resorcinol, 4-((4-phenylamino)azo)benzosulfonic acid sodium salt (Orange IV), 1-((3-aminopropyl)amino)-9,10-anthracenedione (HC Red No. 8), 3',3'',4,5,5',5'',6,7-octabromophenol sulfonephthalein (tetrabromophenol Blue), 1-((4-amino-3,5-dimethylphenyl)(2,6-dichlorophenyl)methylene)-3,5-dimethyl-4-imino-2,5-cyclohexadiene-phosphoric acid (1:1) (Basic Blue 77), 3',3'',5',5''-tetrabromo-m-cresol sulfonephthalein, 2,4-dinitro-1-naphthol-7-sulfonic acid disodium salt (Acid Yellow 1, CI 10316), 4-[2'-hydroxy-1'-naphthyl)azo]benzosulfonic acid sodium salt (Acid Orange 7, CI15510), 3',6'-dihydroxy-2',4',5',7'-tetraiodospiro [isobenzofuran-1 (3H), 9'-(9H)xanthen]-3-one disodium salt (Acid Red 51, Cl45430), 6-hydroxy-5-((2-methoxy-5-methyl-4-sulfophenyl)azo)-2-naphthalenesulfonic acid disodium salt (FD&C Red 40, CI16035), 2,4-dinitro-1-naphthol sodium salt (Acid Yellow 24; Cl10315), 2',4',5',7'-tetrabromo-4,5,6,7-tetrachloro-3',6'-dihydroxyspiro(isobenzofuran-1(3H), 9'-[9H]xanthen]-3-one disodium salt (Acid Red 92; Cl45410), 4-(2-hydroxy-1-naphthylazo)-3-methylbenzenesulfonic acid sodium salt (Acid Orange 8, CI15575), 2-amino-1,4-naphthalenedione, dithizone (1,5-diphenylthiocarbazone), N-((2-hydroxyethyl)-2-nitro-4-trifluoromethyl) aniline (HC Yellow 13), N-(2-hydroxyethyl)-4-nitroaniline and 4-chloro-N-(2,3-dihydroxypropyl)-2-nitroaniline, 1-methyl-4-((methylphenylhydrazono)methyl)pyridinium methylsulfate (Basic Yellow No. 87), 3-((4,5-dihydro-3-methyl-5-oxo-1-phenyl-1H-pyrazol-4-yl)azo)-N,N,N-trimethylbenzenaminium chloride, 3-[(3-methyl-5-hydroxy-1-phenyl-1H-pyrazol-4-yl)azo]-trimethylammoniobenzene chloride (Basic Yellow No. 57), 2-((4-aminophenyl)azo)-1,3-dimethyl-1H-imidazol-3-ium chloride (Basic Orange No. 31), 1,4-dimethyl-5-[(4-(dimethylamino)phenyl)azo]-1,2,4-triazolium chloride (Basic Red No. 22, CI11055), 2-((4-(dimethylamino)-phenyl)azo)-1,3-dimethyl-1H-imidazoium chloride (Basic Red No. 51), 1,4-dimethyl-5-[[4-[methyl (phenylmethyl)amino]-phenyl]azo]-1,2,4-triazolium bromide (Basic Red No. 46), N,N,N-trimethyl-3-{[4-(methylamino)-9,10-dioxo-9,10-dihydro-1-anthracenyl]amino}-1-propanaminium methylsulfate, N,N-dimethyl-3-{[4-(methylamino)-9,10-dioxo-9,10-dihydro-1-anthracenyl] amino}-N-propyl-1-propanaminium chloride and N,N-dimethyl-3-{[4-(methylamino)-9,10-dioxo-9,10-dihydro-1-anthracenyl]amino}-N-propyl-1-propanaminium bromide.

The total content of additional dyes in the colorant according to the invention is from 0.01% to 15% by weight, in particular from 0.1% to 12% by weight.

The oxidation colorant (c) according to the invention, which is mixed prior to application with an oxidizing agent (in particular hydrogen peroxide or its addition compounds) or is oxidized by atmospheric oxygen, comprises in addition to the dyes of the general formula (I), oxidation dye precursors and if necessary one or more of the abovementioned additional direct dyes provided these are stable to the oxidizing agent used.

Suitable oxidation dye precursors are developer substances such as aromatic 1,4-diamines, 4-aminophenol derivatives or pyrazole derivatives, coupler substances such as aromatic 1,3-diamines, 3-aminophenol derivatives, polyphenols or naphtholes and self-coupling compounds.

The total amount of the oxidation dye precursors present in the colorant (c) according to the invention is from 0.01% to 12% by weight, in particular from 0.2% to 6% by weight.

To increase the color intensity, the carriers customary in cosmetic systems can be added if required. Suitable compounds are described, for example, in German Patent No. DE 196 18 595 A1, to which hereby is explicitly referred. Particularly suitable carriers are, for example, benzyl alcohol, vanillin and isovanillin.

For coloring, the dyes described above are applied in a suitable color carrier mass.

The colorant (a), (b), or (c) according to the invention can also comprise all additives customary and known for such preparations, for example, perfume oils, complexing agents, waxes, preservatives, thickeners, antioxidants, alginates, guar gum, haircare substances, such as, for example, cationic polymers or lanolin derivatives, or anionic, nonionic, amphoteric or cationic surface-active substances, Preference is given to using amphoteric or nonionic surface-active substances, for example, betaine surfactants, propionates and glycinates. The above-mentioned constituents are used in the amounts customary for such purposes, for example, the surface-active substances in a concentration of from 0.1% to 30% by weight, and the care substances in an amount of from 0.1% to 5% by weight.

The colorant (a), (b), or (c) according to the invention can, particularly if it is a hair colorant, be present in the form of a powder or granules which is/are dissolved prior to application in an aqueous or aqueous-alcoholic preparation, or else in the form of an aqueous or aqueous-alcoholic solution, a cream, a gel, an emulsion, or an aerosol foam, where the colorant can be formulated either in the form of a single-component preparation or else in the form of a multicomponent preparation, for example, in the form of a two-component preparation in which the particular dye derivative of the general formula (I) is packaged separately from the other constituents and the ready-to-use colorant is only prepared directly prior to application by mixing the two components.

The colorant (a), (b), or (c) according to the invention generally has a pH of 2 to 11, preferably 5 to 10. Both organic and inorganic acids or bases are suitable for adjusting the pH according to the invention.

Depending on the intended use, the colorant according to the invention can be used with one or more synthetic oxidizing agents, for example, hydrogen peroxide or a salt or adduct thereof, as well as persulfates such as sodium persulfate, potassium persulfate or ammonium persulfate (lightening; oxidation colorants), or without a synthetic oxidizing agent (nonoxidative colorants; oxidation by air). Furthermore the colorant may contain an ammonium carbonate, for example, ammonium carbonate or ammonium hydrogen carbonate, or an amino acid or a salt thereof, for example sodium glycinate.

If required, the agent for coloring keratin fibers prior to application is mixed with an oxidizing agent. Suitable oxidizing agents are primarily hydrogen peroxide or its addition compounds onto urea, melamine, sodium borate or sodium carbonate in the form of a 1% to 12% strength, preferably a 3% to 9% strength, aqueous solution. In the case of agents with simultaneous lightening or bleaching, depending on the dye of the formula (I) used it is additionally possible to add persulfates, e.g., ammonium persulfate, potassium persulfate, or sodium persulfate. The weight ratio between color carrier mass and oxidizing agent is here preferably 5:1 to 1:3, in particular 1:1 to 1:2. Larger amounts of oxidizing agent are used especially at higher concentrations of oxidative dye precursors in the colorant, or if greater bleaching of the keratin fibers (in particular of the hair) is intended at the same time.

The colorant according to the invention is generally used by applying an amount of the hair colorant sufficient for the hair coloring, 30 grams to 200 grams depending on hair length, to the hair, allowing the hair colorant to act at 15° C. to 50° C. for 1 minute to 60 minutes, preferably 5 minutes to 30 minutes, then rinsing the hair thoroughly with water, optionally washing with a shampoo and/or after-treating with a hair-conditioning composition and finally drying.

In addition, if no oxidizing agents are added to the coloring mass, the above described colorant can comprise natural or synthetic polymers or modified polymers of natural origin customary for cosmetic compositions, as a result of which setting of the hair is achieved at the same time as the coloring. Such compositions are generally referred to as tinting setting compositions or color setting compositions.

Of the synthetic polymers known for this purpose in cosmetics, mention may be made, for example, of polyvinylpyrrolidone, polyvinyl acetate, polyvinyl alcohol or polyacrylic compounds, such as polyacrylic acid or polymethacrylic acid, basic polymers of esters of polyacrylic acid, polymethylacrylic acid, and amino alcohols, for example, salts or quaternization products thereof, polyacrylonitrile, polyvinyl acetates, and copolymers of such compounds, such as, for example, polyvinylpyrrolidone-vinyl acetate; while natural polymers or modified natural polymers which can be used are, for example, chitosan (deacetylated chitin) or chitosan derivatives.

The abovementioned polymers may be present in the colorant (a) according to the invention in the amounts customary for such agents, in particular in an amount of from 1% to 5% by weight. The pH of the tinting setting composition or color setting composition according to the invention is preferably 4 to 10.

The hair colorant with additional setting is used in a known and customary manner by wetting the hair with the setting composition, arranging (styling) the hair into the hairstyle and then drying.

The colorant with pendant cationic azodyes of the formula (I) permits, inter alia, a simple and gentle coloration of hair with varying degrees of damage (for example, recolorations of sections of hair which have already been oxidatively colored), the color carrier mass without oxidizing agent—neat or mixed with an acidic, neutral or basic aqueous diluent—being applied to the predamaged sections of hair (for example, the hair ends), while the color carrier mass mixed with the oxidizing agent is applied to the sections of hair with little or no predamage (for example, the new hair growth). The aqueous component used for dilution can comprise the abovementioned customary additives for solutions, creams, emulsions, or gels. This process allows colorations matched to the nature of the hair which are characterized by a hair-gentle evening out between roots and ends, which is not possible when using customary oxidative hair colorants since an oxidizing agent is always required to couple the dye precursors.

The colorant according to the invention permits a coloration of keratin fibers, in particular of human hair, with very strong color intensity and brilliance, a good eveness of color between damaged and undamaged hair (such as, for example, between hair ends and new hair growth), very good durability (washing fastness), very good mildness to the hair and variable application options with and without oxidizing agents.

The dyes of formula (I) can be prepared analogously to known preparation processes, such as, for example, in a one step procedure, via diazotation of 1,3-thiazol-2-amine, 1H-imidazol-2-amine, 1,2,4-thiadiazol-5-amine, 1,3,4-thiadiazol-2-amine, 4H-1,2,4-triazol-3-amine, or the like, and coupling with cationic aniline derivatives, or in a 2-step procedure via diazotation of 1,3-thiazol-2-amine, 1H-imidazol-2-amine, 1,2,4-thiadiazol-5-amine, 1,3,4-thiadiazol-2-amine, 4H-1,2,4-triazol-3-amine, or the like, and coupling with bromoalkyl-aniline derivatives, followed by quaternization with heterocycles.

Some dyes of the formula (I) are known as textile dyes.

The examples below are intended to illustrate the subject-matter of the invention in more detail without limiting it thereto.

EXAMPLES

Example 1

Example 1a

1-{2-[{4-[(4,5-dimethyl-1,3-thiazol-2-yl)diazenyl]-phenyl}(ethyl)amino]ethyl}-3-methyl-1H-imidazol-3-ium bromide Step 1: Azocoupling (Standard Procedure)

2.0 g (12.1 mmol) 2-amino-4,5-dimethyl-1,3-thiazol hydrochloride is dissolved in a mixture containing 50 ml acetic acid and 1.8 g sulphuric acid while the temperature rises up to 30° C. The suspension is cooled to 15° C. followed by dropwise addition of 5.8 g of 40% aqueous nitrosyl sulphuric acid and stirred for 2 hours. In a separate beaker a solution of 2.80 g N-(2-bromoethyl)-N-ethylaniline in a mixture of 15 ml acetic acid, 1.4 g hydrochloric acid and 20 g ice is prepared. The previously prepared diazonium salt solution is added slowly to this solution so that the temperature does not exceed 5° C. The reaction mixture is further stirred for 1 hour at 5° C. and then for 2 hours at room temperature. The pH value is adjusted to 4 by adding an appropriate amount of 30% aqueous sodium hydroxide. The resulted precipitate was filtered off, washed with water, and dried in vacuum at 40° C.

After recrystallization in methanol/water 3.02 g N-(2-bromoethyl)-4-[(4,5-dimethyl-1,3-thiazol-2-yl)diazenyl]-N-ethylaniline were obtained as red crystals.

$^1$H NMR (300 MHz, DMSO): δ=7.76 (d, J=9.0, 2H, H(3) and H(5)-phenyl); 6.89 (d, J=9.0, 2H, H(2) and H(6)-phenyl); 3.84 (t, J=6.9, 2H, CH2); 3.65 (t, J=6.9, 2H, CH2); 3.58 (q, J=6.9, 2H, CH2); 2.37 (s, 3H, CH3); 2.32 (s, 3H, CH3); 1.16 (t, J=6.9, 3H, CH3).

Step 2: Quaternization (Standard Procedure)

0.5 g N-(2-bromoethyl)-4-[(4,5-dimethyl-1,3-thiazol-2-yl)diazenyl]-N-ethylaniline is dissolved in 10 ml acetonitrile followed by subsequent addition of 5.3 g 1-methyl-1H-imidazole. The reaction mixture is heated at 80° C. overnight. After cooling to room temperature, the formed precipitate is filtered off, washed with acetonitrile, and dried under vacuum at 40° C. 0.49 g of 1-{2-[{4-[(4,5-dimethyl-1,3-thiazol-2-yl)diazenyl]phenyl}(ethyl)amino]ethyl}-3-methyl-1H-imidazol-3-ium bromide are obtained as a red crystals.

$^1$H NMR (300 MHz, DMSO): δ=9.17 (s, 1H, H(2)-imidazol); 7.85 (s, 1H, imidazol); 7.74 (d, J=9.3, 2H, H(3) and H(5)-phenyl); 7.71 (s, 1H, imidazol); 6.89 (d, J=9.3, 2H, H(2) and H(6)-phenyl); 4.45 (t, J=6.0, 2H, CH2); 3.89 (t, J=6.0, 2H, CH2); 3.83 (s, 3H, N$^+$CH3); 3.44 (q, J=6.9, 2H, CH2); 2.38 (s, 3H, CH3); 2.32 (s, 3H, CH3); 1.10 (t, J=6.9, 3H, CH3).

CHN Analysis:

| ($C_{19}H_{25}N_6S*Br$) | % C | % H | % N | % S |
|---|---|---|---|---|
| calculated | 50.78 | 5.61 | 18.70 | 7.14 |
| found | 50.80 | 5.57 | 18.84 | 7.27 |

Example 1b

1-[2-(ethyl{4-[1,3-thiazol-2-yldiazenyl]phenyl}amino)ethyl]-3-methyl-1H-imidazol-3-ium Bromide Analogously to the procedure described in example 1a, by azocoupling of 2-amino-1,3-thiazol with N-(2-bromoethyl)-N-ethylaniline to give N-(2-bromoethyl)-N-ethyl-4-[1,3-thiazol-2-yldiazenyl]aniline in 73% yield, followed by quaternization with 1-methyl-1H-imidazole to give 1-[2-(ethyl{4-[1,3-thiazol-2-yldiazenyl]phenyl}amino)ethyl]-3-methyl-1H-imidazol-3-ium bromide in 68% yield.

$^1$H NMR (300 MHz, DMSO): δ=9.17 (s, 1H, H(2)-imidazol); 7.97 (d, J=4.2, 1H, H(4)-thiazol); 7.85 (s, 1H, imidazol); 7.80 (d, J=9.0, 2H, H(3) and H(5)-phenyl); 7.72 (d, J=4.2, 1H, H(5)-thiazol); 7.71 (s, 1H, imidazol); 6.91 (d, J=9.0, 2H, H(2) and H(6)-phenyl); 4.44 (t, J=6.0, 2H, CH2); 3.91 (t, J=6.0, 2H, CH2); 3.83 (s, 3H, N$^+$CH3); 3.46 (q, J=6.9, 2H, CH2); 1.11 (t, J=6.9, 3H, CH3).

Example 1c

1-[2-(ethyl{4-[(5-methyl-1,3-thiazol-2-yl)diazenyl]phenyl}amino)ethyl]-3-methyl-1H-imidazol-3-ium Bromide Analogously to the procedure described in example 1a, by azocoupling of 2-amino-5-methyl-1,3-thiazol with N-(2-bromoethyl)-N-ethylaniline to give N-(2-bromoethyl)-N-ethyl-4-[(5-methyl-1,3-thiazol-2-yl)diazenyl]aniline in 81% yield, followed by quaternization with 1-methyl-1H-imidazole to give 1-[2-(ethyl{-4-[(5-methyl-1,3-thiazol-2-yl)diazenyl]phenyl}amino)ethyl]-3-methyl-1H-imidazol-3-ium bromide in 96% yield.

$^1$H NMR (300 MHz, DMSO): δ=9.15 (s, 1H, H(2)-imidazol); 7.84 (s, 1H, imidazol); ); 7.76 (d, J=9.3, 2H, H(3) and H(5)-phenyl); 7.71 (s, 1H, imidazol); 7.70 (s, 1H, H(4)-thiazol); 6.90 (d, J=9.3, 2H, H(2) and H(6)-phenyl); 4.42 (t, J=6.0, 2H, CH2); 3.90 (t, J=6.0, 2H, CH2); 3.83 (s, 3H, N$^+$CH3); 3.45 (q, J=6.9, 2H, CH2); 2.48 (s, 3H, CH3); 1.11 (t, J=6.9, 3H, CH3).

Example 1d

1-{2-[{4-[(4,5-dimethyl-1,3-thiazol-2-yl)diazenyl]-3-methylphenyl}(ethyl)amino]ethyl}-3-methyl-1H-imidazol-3-ium Bromide Analogously to the procedure described in example 1a, by azocoupling of 2-amino-4,5-methyl-1,3-thiazol hydrochloride with N-(2-bromoethyl)-N-ethyl-3-methylaniline to give N-(2-bromoethyl)-4-[(4,5-dimethyl-1,3-thiazol-2-yl)diazenyl]-N-ethyl-3-methylaniline in 67% yield, followed by quaternization with 1-methyl-1H-imidazole to give 1-{2-[{4-[(4,5-dimethyl-1,3-thiazol-2-yl)diazenyl]-3-methylphenyl}(ethyl)amino]ethyl}-3-methyl-1H-imidazol-3-ium bromide in 82% yield.

$^1$H NMR (300 MHz, DMSO): δ=9.15 (s, 1H, H(2)-imidazol); 7.84 (s, 1H, imidazol); 7.71 (s, 1H, imidazol); 7.65 (d, J=9.3, 1H, H(5)-phenyl); 6.72 (d, J=9.3, 1H, H(6)-phenyl); 6.67 (s, 1H, H(2)-phenyl); 4.42 (t, J=6.0, 2H, CH2); 3.88 (t, J=6.0, 2H, CH2); 3.83 (s, 3H, N$^+$CH3); 3.43 (q, J=6.9, 2H, CH2); 2.54 (s, 3H, CH3); 2.37 (s, 3H, CH3); 2.31 (s, 3H, CH3); 1.10 (t, J=6.9, 3H, CH3). API-ES MS: 383 [M$^+$] (100)

Example 1e

1-[2-(ethyl{4-[(6-nitro-1,3-benzothiazol-2-yl)diazenyl]-phenyl}amino)ethyl]-3-methyl-1H-imidazol-3-ium Bromide Analogously to the procedure described in example 1a, by azocoupling of 6-nitro-1,3-benzothiazol-2-amine with N-(2-bromoethyl)-N-ethylaniline to give N-(2-bromoethyl)-N-ethyl-4-[(6-nitro-1,3-benzothiazol-2-yl)diazenyl]-aniline in 45% yield, followed by quaternization with 1-methyl-1H-imidazole to give 1-[2-(ethyl{4-[(6-nitro-1,3-benzothiazol-2-yl)diazenyl]-phenyl}amino)ethyl]-3-methyl-1H-imidazol-3-ium bromide in 41% yield.

$^1$H NMR (300 MHz, DMSO): δ=9.25 br (s, 1H, imidazol), 9.06 (s, 1H), 8.32 (d, J=8.7, 1H), 8.16 (d, J=9.0, 1H), 7.88-7.89 (m, 1H, imidazol, overlap), 7.88 (d, J=6.6, 2H, phenyl), 7.70-7.73 (m, 1H, imidazol), 6.99 (d, J=6.6, 2H, phenyl), 4.00-4.49 (m, 4H, 2×CH$_2$), 3.85 (s, 3H, CH$_3$), 3.50-3.54 (m, 2H, CH$_2$), 1.13-1.15 (m, 3H CH$_3$).

Example 1f

1-{2-[{4-[(4-chloro-5-nitro-1,3-thiazol-2-yl)diazenyl]-phenyl}(ethyl)amino]ethyl}-3-methyl-1H-imidazol-3-ium Bromide Step 1: Azocoupling 1.00 g 4-chloro-5-nitro-1,3-thiazol-2-ylamine is diazotized in a mixture containing 15 ml phosphoric acid, 3.2 g hydrochloric acid and 0.46 g sodium nitrate at −10° C. Azo coupling was performed by adding the diazonium solution to a mixture of 1.32 g N-(2-bromoethyl)-N-ethylaniline in 15 ml acetic acid. After stirring for 4 hours the resulting precipitate is filtered off washed with water, and dried in vacuum at 40° C.

1.20 g N-(2-bromoethyl)-4-[(4-chloro-5-nitro-1,3-thiazol-2-yl)diazenyl]-N-ethylaniline is obtained as a dark red powder.

$^1$H NMR (300 MHz, DMSO): δ=7.79 (d, J=8.7, 2H, phenyl) 6.96 (d, J=9.3, 2H, phenyl), 3.92-3.88 (m, 2H, CH$_2$), 3.74-3.58 (m, 4H, 2×CH$_2$), 1.13 (t, J=6.9, 3H, CH$_3$).

Step 2: Quaternization 1.20 g N-(2-bromoethyl)-4-[(4-chloro-5-nitro-1,3-thiazol-2-yl)diazenyl]-N-ethylaniline is dissolved in 20 ml acetonitrile followed by subsequent addition of 5.99 g 1-methyl-1H-imidazole. The reaction mixture is stirred under reflux for 3 days and allowed to cool to room temperature. The resulted precipitate is filtered off, washed with acetonitrile, and dried in vacuum at 40° C. 0.43 g 1-{2-[{4-[(4-chloro-5-nitro-1,3-thiazol-2-yl)diazenyl]phenyl}(ethyl)amino]ethyl}-3-methyl-1H-imidazol-3-ium bromide is obtained as a bordeaux red powder.

$^1$H NMR (300 MHz, DMSO): δ=9.22 (s, 1H, imidazol), 7.86-7.85 (m, 1H, imidazol), 7.79 (d, J=9.0, 2H, phenyl), 7.71-7.70 (m, 1H, imidazol), 6.95 (d, J=9.3, 2H, phenyl), 4.45-4.43 (m, 2H, CH$_2$), 3.98-3.96 (m, 2H, CH$_2$), 3.83 (s, 3H, N—CH$_3$), 3.68-3.65 (m, 2H, CH$_2$), 1.12 (t, J=6.6, 3H, CH$_3$).

Example 1g

1-[2-(ethyl{4-[1H-[1,3]thiazolo[5,4-f]indazol-6-yldiazenyl]-phenyl}amino)ethyl]-3-methyl-1H-imidazol-3-ium Bromide Analogously to the procedure described in example 1f, by azocoupling of 1H-[1,3]thiazolo[5,4-f]indazol-6-amine with N-(2-bromoethyl)-N-ethylaniline to give N-(2-bromoethyl)-N-ethyl-4-[1H-[1,3]thiazolo[5,4-f]indazol-6-yldiazenyl] aniline in 56% yield, followed by quaternization with 1-methyl-1H-imidazole to give 1-[2-(ethyl{4-[1H-[1,3]thiazolo[5,4-f]indazol-6-yldiazenyl]phenyl}amino)ethyl]-3-methyl-1H-imidazol-3-ium bromide in 49% yield.

$^1$H NMR (300 MHz, DMSO): δ=9.22 (s, br, 1H, imidazol), 8.28 (s, 1H, N—H), 7.88-7.86 (m, 4H, phenyl/imidazol, overlap), 7.76-7.73 (m, 2H), 6.98 (d, J=9.0, 2H, phenyl), 4.47-4.44 (m, 2H, CH$_2$), 3.96-3.95 (m, 2H, CH$_2$), 3.84 (s, 3H, N—CH$_3$), 3.52-3.50 (m, 2H, CH$_2$), 1.14 (t, J=6.0, 3H, CH$_3$).

Example 1h

1-{2-[{4-[(5-chloro[1,3]thiazolo[5,4-b]pyridin-2-yl)diazenyl]-phenyl}(ethyl)amino]ethyl}-3-methyl-1H-imidazol-3-ium Bromide Analogously to the procedure described in example 1f, by azocoupling of 5-chloro[1,3]thiazolo[5,4-b]pyridin-2-amine with N-(2-bromoethyl)-N-ethylaniline to give N-(2-bromoethyl)-4-[(E)-(5-chloro[1,3]thiazolo-[5,4-b]pryridin-2-yl)diazenyl]-N-ethylaniline in 42% yield, followed by quaternization with 1-methyl-1H-imidazole to give 1-{2-[{4-[(5-chloro[1,3]thiazolo[5,4-b]pyridin-2-yl)diazenyl]phenyl}(ethyl)amino]ethyl}-3-methyl-1H-imidazol-3-ium bromide in 10% yield.

$^1$H NMR (300 MHz, DMSO): δ=9.18 (s, 1H, imidazol), 8.42 (d, J=8.7, 1H, pyridylthiazol), 7.88 (d, J=9.0, 2H, phenyl), 7.86-7.84 (m, 1H, imidazol), 7.71-7.70 (m, 1H, imidazol), 7.67 (d, J=8.7, 1H, pyridylthiazol), 6.99 (d, J=9.0, 2H, phenyl), 4.47-4.43 (m, 2H, CH$_2$), 3.98-3.95 (m, 2H, CH$_2$), 1.15 (t, 3H, J=6.6 Hz, CH$_3$).

Example 1i

1-{2-[ethyl(4-{[5-(methyloxy)[1,3]thiazolo[5,4-b]pyridin-2-yl]diazenyl}phenyl)amino]ethyl}-3-methyl-1H-imidazol-3-ium Bromide Analogously to the procedure described in example 1a, by azocoupling of 5-methoxy[1,3]thiazolo[5,4-b]pyridin-2-amine with N-(2-bromoethyl)-N-ethylaniline to give N-(2-bromoethyl)-N-ethyl-4-[(E)-(5-methoxy[1,3]-thiazolo[5,4-b]pyridin-2-yl)diazenyl]aniline in 51% yield, followed by quaternization with 1-methyl-1H-imidazole to give 1-{2-[ethyl(4-{[5-(methyloxy)[1,3]thiazolo[5,4-b]pyridin-2-yl]diazenyl}phenyl)amino]ethyl}-3-methyl-1H-imidazol-3-ium bromide in 15% yield.

$^1$H NMR (300 MHz, DMSO): δ=9.20 (s, 1H, imidazol), 8.30 (d, J=9.0, 1H, pyridylthiazol), 7.85-7.82 (m, 3H, imidazol/phenyl, overlap), 7.71 (s, 1H), 7.02 (d, J=8.7, 1H, pyridylthiazol), 6.96 (d, J=8.7, 2H, phenyl), 4.46-4.42 (m, 2H, CH$_2$), 3.97-3.93 (m, 5H, CH3+CH$_2$), 3.51-3.49 (m, 2H, CH$_2$), 1.13 (t, J=6.6, 3H, CH$_3$).

Example 1j

1-[2-(ethyl{4-[(1-methyl-1H-imidazol-2-yl)diazenyl]-phenyl}amino)ethyl]-3-methyl-1H-imidazol-3-ium Bromide Step 1: Azocoupling 1.32 g 2-amino-1H-imidazol-hemisulfate is diazotized in a mixture containing 2 ml hydrochloric acid, 2 ml acetic acid, 12 ml water and 0.7 g sodium nitrate at 5° C. Azo coupling is performed by adding 2.3 g N-(2-bromoethyl)-N-ethylaniline to the above diazonium solution. After stirring for 2 hours at room temperature the mixture is poured on 50 ml saturated sodium bicarbonate. The resulted precipitate is filtered off, washed with water, and dried in vacuum at 40° C. After chromatography on silicagel with ethylacetate, 0.6 g N-(2-bromoethyl)-N-ethyl-4-[(E)-1H-imidazol-2-yldiazenyl]aniline is obtained as a brown powder.

$^1$H NMR (300 MHz, DMSO): δ=12.5 (br s, 1H, NH); 7.76 (d, J=9.0, 2H, phenyl); 7.2 (s, 2H, imidazol); 6.87 (d, J=9.0, 2H, phenyl); 3.81 (t, J=6.9, 2H, CH2); 3.65 (t, J=6.9, 2H, CH2); 3.55 (q, J=6.9, 2H, CH2); 1.16 (t, J=6.9, 3H, CH3).

Step 2: Quaternization 0.22 g N-(2-bromoethyl)-N-ethyl-4-[(E)-1H-imidazol-2-yldiazenyl]aniline is dissolved in 4.5 ml acetonitrile followed by subsequent addition of 2.6 g 1-methyl-1H-imidazole. The reaction mixture is stirred overnight under reflux and allowed to cool to room temperature. It is diluted with 45 ml acetone and 20 ml ethylacetate. The resulted precipitate is filtered off and dried in vacuum at 40° C.

0.28 g 1-[2-(ethyl{4-[1H-imidazol-2-yldiazenyl]-phenyl}amino)ethyl]-3-methyl-1H-imidazol-3-ium bromide is obtained as a red powder.

Step 3: Alkylation

To a solution of 0.12 g 1-[2-(ethyl{4-[1H-imidazol-2-yldiazenyl]phenyl}amino)ethyl]-3-methyl-1H-imidazol-3-ium bromide in 5 ml methanol is added 35 mg sodium hydroxide and 0.45 g dimethylsulfate. The mixture is stirred three days under reflux. After evaporation of the solvent, the crude product is treated with ethylacetate and acetone.

0.36 g of 1-[2-(ethyl{4-[(1-methyl-1H-imidazol-2-yl)diazenyl]phenyl}amino)ethyl]-3-methyl-1H-imidazol-3-ium bromide is obtained as red powder.

$^1$H NMR (300 MHz, DMSO): δ=9.15 (s, 1H, H(2)-imidazol); 7.91 (d, J=9.3, 2H, phenyl); 7.84 (s, 1H, imidazol); 7.78 (s, 2H, H(4) and H(5) imidazol); 7.71 (s, 1H, imidazol); 7.00 (d, J=9.3, 2H, phenyl); 4.47 (t, J=6.6, 2H, CH2); 3.98 (m, 2H, CH2); 3.98 (s, 3H, N—CH3); 3.84 (s, 3H, N$^+$CH3); 3.52 (q, J=6.6, 2H, CH2); 2.51 (s, 3H, CH3); 1.14 (t, J=6.6, 3H, CH3). API-ES MS: 324 [M$^+$] (100)

Examples 2 to 11

Hair Colorant

| | |
|---|---|
| 0.33 g | Dye of the formula (I) |
| 5.0 g | Ethanol |
| 4.0 g | Decyl glucoside |
| 0.2 g | Ethylenediaminotetraacetic acid disodium salt |
| balance to 100.0 g | Water, demineralized |

If necessary, the coloring solution is adjusted to the pH values given in Table 1 by adding ammonia.

The hair coloring is carried out by applying an amount of the colorant sufficient for the hair coloring to the hair and distributing it evenly using a brush. After a contact time of 30 minutes at 40° C., the hair is rinsed with lukewarm water, washed with a shampoo, rinsed with lukewarm water, and then dried.

The coloring results are summarized in Table 1 below.

TABLE 1

| Ex. | Compound of the formula (I) (as in examples 1a-1j) | pH of the colorant | Color-shade after coloring | Color-measurement values after coloring |
|---|---|---|---|---|
| — | Color shade of the hair before the coloring treatment | — | — | L = 80.60<br>C = 12.10<br>h = 92.10 |
| 2 | 1-{2-[{4-[(4,5-dimethyl-1,3-thiazol-2-yl)diazenyl]phenyl}-(ethyl)amino]ethyl}-3-methyl-1H-imidazol-3-ium bromide (1a) | 9.1 | red-orange | L = 41.87<br>C = 66.73<br>h = 38.8 |
| 3 | 1-[2-(ethyl{4-[1,3-thiazol-2-yldiazenyl]phenyl}amino)ethyl]-3-methyl-1H-imidazol-3-ium bromide (1b) | 9.4 | red-orange | L = 45.14<br>C = 71.57<br>h = 42.1 |
| 4 | 1-[2-(ethyl{4-[(5-methyl-1,3-thiazol-2-yl)diazenyl]phenyl}-amino)ethyl]-3-methyl-1H-imidazol-3-ium bromide (1c) | 9.2 | red-orange | L = 44.69<br>C = 70.61<br>h = 42.4 |
| 5 | 1-{2-[{4-[(4,5-dimethyl-1,3-thiazol-2-yl)diazenyl]-3-methylphenyl}(ethyl)amino]ethyl}-3-methyl-1H-imidazol-3-ium bromide (1d) | 9.2 | red | L = 41.34<br>C = 62.46<br>h = 35.1 |
| 6 | 1-[2-(ethyl{4-[(6-nitro-1,3-benzothiazol-2-yl)diazenyl]-phenyl}amino)ethyl]-3-methyl-1H-imidazol-3-ium bromide (1e) | 9.8 | violet | L = 22.53<br>C = 30.32<br>h = 358.9 |

TABLE 1-continued

| Ex. | Compound of the formula (I) (as in examples 1a-1j) | pH of the colorant | Color-shade after coloring | Color-measurement values after coloring |
|---|---|---|---|---|
| 7 | 1-{2-[{4-[(4-chloro-5-nitro-1,3-thiazol-2-yl)diazenyl]-phenyl}(ethyl)amino]ethyl}-3-methyl-1H-imidazol-3-ium bromide (1f) | 9.8 | pink | L = 30.77<br>C = 42.35<br>h = 11.78 |
| 8 | 1-[2-(ethyl{4-[1H-[1,3]thiazolo[5,4-f]indazol-6-yldiazenyl]phenyl}amino)ethyl]-3-methyl-1H-imidazol-3-ium bromide (1g) | 9.8 | bordeaux | L = 27.62<br>C = 46.46<br>h = 18.82 |
| 9 | 1-{2-[{4-[(5-chloro[1,3]-thiazolo[5,4-b]pyridin-2-yl)diazenyl]phenyl}(ethyl)amino]ethyl}-3-methyl-1H-imidazol-3-ium bromide (1h) | 9.8 | red-blue | L = 33.69<br>C = 57.48<br>h = 23.07 |
| 10 | 1-{2-[ethyl(4-{[5-(methyloxy)-[1,3]thiazolo[5,4-b]pyridin-2-yl]diazenyl}phenyl)amino]ethyl}-3-methyl-1H-imidazol-3-ium bromide (1i) | 9.8 | pink | L = 32.90<br>C = 52.05<br>h = 12.67 |
| 11 | 1-[2-(ethyl{4-[(1-methyl-1H-imidazol-2-yl)diazenyl]-phenyl}amino)ethyl]-3-methyl-1H-imidazol-3-ium bromide (1j) | 8.8 | cherry-red | L = 37.11<br>C = 60.52<br>h = 27.9 |

Example 12

Hair Colorant with Cationic Surface-Active Substances

| | |
|---|---|
| 0.33 g | 1-{2-[{4-[(4,5-dimethyl-1,3-thiazol-2-yl)-diazenyl]phenyl}(ethyl)amino]ethyl}-3-methyl-1H-imidazol-3-ium bromide (1a) |
| 5.00 g | Ethanol |
| 4.00 g | Cetyltrimethylammonium chloride, 25% in water |
| balance to 100.00 g | Water, demineralized |

The pH is adjusted to 9.3 using 25% strength ammonia.

The hair coloring is carried out by applying an amount of the colorant sufficient for the hair coloring to the hair and distributing it evenly using a brush. After a contact time of 30 minutes at 40° C., the hair (L=80.6; C=12.1; h=92.1) is rinsed with lukewarm water, washed with a shampoo, rinsed again with lukewarm water, and then dried.

This gives an intensely red-orange colored switch (L=43.96; C=67.24; h=40.1).

Example 13

Hair Colorant with Amphoteric Surface-Active Substances

| | |
|---|---|
| 0.33 g | 1-{2-[{4-[(4,5-dimethyl-1,3-thiazol-2-yl)-diazenyl]phenyl}(ethyl)amino]ethyl}-3-methyl-1H-imidazol-3-ium bromide (2a) |
| 5.00 g | Ethanol |
| 7.50 g | Coconut fatty acid amidopropylbetaine |
| Balance to 100.00 g | Water, demineralized |

The pH is adjusted to 9.1 using 25% strength ammonia.

The hair coloring is carried out by applying an amount of the colorant sufficient for the hair coloring to the hair and distributing it evenly using a brush. After a contact time of 30 minutes at 40° C., the hair (L=80.6; C=12.1; h=92.1) is rinsed with lukewarm water, washed with a shampoo, rinsed again with lukewarm water, and then dried.

This gives an intensely red-orange colored switch (L=45.07; C=65.53; h=41.40).

Examples 14 to 21

Hair Colorant with Oxidizing Agent

| | |
|---|---|
| 0.66 g | Dye of the formula (I) as in table 2 |
| 5.0 g | Ethanol |
| 4.0 g | Decyl glucoside |
| 0.2 g | Ethylenediaminotetraacetic acid disodium salt |
| Balance to 00.0 g | Water, demineralized |

5 g of the above color carrier mass is mixed with 5 g of a 9% strength hydrogen peroxide solution. The pH is adjusted to the basic pH values given in Table 2, using 25% strength ammonia.

The resulting ready-to-use hair colorant is applied to the hair and distributed evenly using a brush. After a contact time of 30 minutes at 40° C., the hair is rinsed with lukewarm water, washed with a shampoo, rinsed again with lukewarm water, and then dried.

The coloring results are summarized in Table 2 below.

TABLE 2

| Ex. | Compound of the formula (I) (as in examples 1a-1j) | pH of the colorant | Color shade after coloring | Color measurement values after coloring |
|---|---|---|---|---|
| — | Color shade of the hair before the coloring treatment | — | — | L = 80.60<br>C = 12.10<br>h = 92.10 |
| 14 | 1-{2-[{4-[(4,5-dimethyl-1,3-thiazol-2-yl)diazenyl]phenyl}-(ethyl)amino]ethyl}-3-methyl-1H-imidazol-3-ium bromide (1a) | 9.1 | red-orange | L = 44.66<br>C = 69.35<br>h = 40.0 |
| 15 | 1-[2-(ethyl{4-[1,3-thiazol-2-yldiazenyl]phenyl}amino)ethyl]-3-methyl-1H-imidazol-3-ium bromide (1b) | 9.4 | red-orange | L = 46.28<br>C = 72.81<br>h = 42.2 |
| 16 | 1-[2-(ethyl{4-[(5-methyl-1,3-thiazol-2-yl)diazenyl]phenyl}-amino)ethyl]-3-methyl-1H-imidazol-3-ium bromide (1c) | 9.2 | red-orange | L = 45.43<br>C = 73.28<br>h = 42.3 |
| 17 | 1-{2-[{4-[(4,5-dimethyl-1,3-thiazol-2-yl)diazenyl]-3-methylphenyl}(ethyl)amino]ethyl}-3-methyl-1H-imidazol-3-ium bromide (1d) | 9.2 | red | L = 40.07<br>C = 66.77<br>h = 34.2 |
| 18 | 1-[2-(ethyl{4-[(6-nitro-1,3-benzothiazol-2-yl)diazenyl]-phenyl}amino)ethyl]-3-methyl-1H-imidazol-3-ium bromide (1e) | 9.8 | violet | L = 25.38<br>C = 38.11<br>h = 354.1 |
| 19 | 1-[2-(ethyl{4-[1H-[1,3]thiazolo-[5,4-f]indazol-6-yldiazenyl]-phenyl}amino)ethyl]-3-methyl-1H-imidazol-3-ium bromide (1g) | 9.8 | bordeaux | L = 32.53<br>C = 51.88<br>h = 16.8 |
| 20 | 1-{2-[ethyl(4-{[5-(methyloxy)-[1,3]thiazolo[5,4-b]pyridin-2-yl]diazenyl}phenyl)amino]ethyl}-3-methyl-1H-imidazol-3-ium bromide (1i) | 9.8 | red-blue | L = 36.18<br>C = 61.56<br>h = 23.2 |
| 21 | 1-[2-(ethyl{4-[(1-methyl-1H-imidazol-2-yl)diazenyl]phenyl}-amino)ethyl]-3-methyl-1H-imidazol-3-ium bromide (1j) | 9.0 | cherry-red | L = 35.29<br>C = 62.92<br>h = 28.3 |

Examples 22

Hair Colorant without Oxidizing Agent

| | |
|---|---|
| 0.33 g | Dye of the formula (I) as in Table 3 |
| 5.0 g | Ethanol |
| 4.0 g | Decyl glucoside |
| 0.2 g | Ethylenediaminotetraacetic acid disodium salt |
| balance to 100.0 g | Water, demineralized |

The pH is adjusted to the given pH in Table 3 using 25% strength ammonia.

The resulting ready-to-use hair colorant is applied to natural hair (L=34.24, C=14.62, h=66.7) and distributed evenly using a brush. After a contact time of 30 minutes at 40° C., the hair is rinsed with lukewarm water, washed with a shampoo, rinsed again with lukewarm water, and then dried. The washing process is repeated five times. The colors do not change visually.

TABLE 3

| Ex. | Compound of the formula (I) | pH of the colorant | Color shade after coloring | Color shade after washing |
|---|---|---|---|---|
| 22 | 1-{2-[{4-[(4,5-dimethyl-1,3-thiazol-2-yl)diazenyl]phenyl}-(ethyl)amino]ethyl}-3-methyl-1H-imidazol-3-ium bromide (1a) | 9.4 | mahogany<br>L = 27.24<br>C = 22.25<br>h = 39.9 | mahogany<br>L = 29.43<br>C = 22.53<br>h = 45.2 |

Examples 23

Hair Colorant with Oxidizing Agent

| | |
|---|---|
| 0.66 g | Dye of the formula (I) as in table 4 |
| 5.0 g | Ethanol |
| 4.0 g | Decyl glucoside |
| 0.2 g | Ethylenediaminotetraacetic acid disodium salt |
| balance to 100.0 g | Water, demineralized |

5 g of the above color carrier mass is mixed with 5 g of a 9% strength hydrogen peroxide solution. The pH is adjusted to the given pH in Table 4 using 25% strength ammonia.

The resulting ready-to-use hair colorant is applied to natural hair (L=34.24, C=14.62, h=66.7) and distributed evenly using a brush. After a contact time of 30 minutes at 40° C., the hair is rinsed with lukewarm water, washed with a shampoo, rinsed again with lukewarm water, and then dried. The washing process is repeated five times. The colors do not change visually.

TABLE 4

| Ex. | Compound of the formula (I) | pH of the colorant | Color shade after coloring | Color shade after washing |
|---|---|---|---|---|
| 23 | 1-{2-[{4-[(4,5-dimethyl-1,3-thiazol-2-yl)diazenyl]phenyl}-(ethyl)amino]ethyl}-3-methyl-1H-imidazol-3-ium bromide (1a) | 9.4 | mahogany-orange L = 29.04 C = 25.99 h = 41.8 | mahogany-orange L = 30.07 C = 25.29 h = 44.7 |

The L*C*h* color measurement values given in the preceding examples are measured using a calorimeter from Minolta, model Chromameter II. The L value is the lightness (i.e., the lower the L value, the greater the color intensity), while the C value is a measure of the colorfulness ("chroma") (i.e., the greater the C value, the more colorful the color). The h value is the color shade angle ("hue").

Unless stated otherwise, all of the percentages given in the present application are percentages by weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A keratin dyeing composition comprising:
(a) a medium suitable for dyeing;
(b) at least one azodye of the general formula (I):

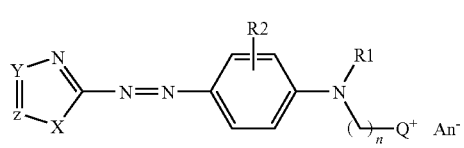

wherein

X is selected from the group consisting of oxygen, sulfur, N—R3 and C—R4;

Y is selected from the group consisting of C—R5, nitrogen, N—R6, sulfur and oxygen;

Z is C—R7 or nitrogen;

with the proviso that the heterocycle of the formula (I) comprises at least two and at most three heteroatoms, where the heterocycle has at most one sulfur atom or one oxygen atom;

n is an integer from 1 to 6;

R1 is selected from the group consisting of hydrogen, a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;

R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;

or if Y and Z are C—R5 and C—R7, the radical groups R5 and R7, together with the remaining molecule, can form a heterocyclic or carbocyclic, saturated or unsaturated, substituted or unsubstituted ring system;

or if X and Y are C—R4 and C—R5, the radical groups R4 and R5, together with the remaining molecule, can form a heterocyclic or carbocyclic, saturated or unsaturated, substituted or unsubstituted ring system;

R3 and R6 may be identical or different and, independently of one another, are selected from the group consisting of a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group and a substituted or unsubstituted benzyl group;

Q+ represents an aromatic or non aromatic, substituted or unsubstituted 4- to 6-membered heterocyclic quaternary ammonium group, which may contain other heteroatoms selected from the group consisting of nitrogen, sulfur and oxygen, with the proviso that the cationic heterocycle comprises at most three heteroatoms, where the heterocycle has at most one sulfur atom or oxygen atom;

or the radical group R1, together with Q+, can form a 5 or 6-membered unsaturated heterocyclic, substituted or unsubstituted cationic ring system;

the anion An- is an organic or inorganic acid anion and (c) at least one additional direct dye which is selected from the group consisting of nitro dyes, azodyes, anthraquinone dyes, triphenylmethane dyes, basic dyes and acidic dyes.

2. A method of coloring keratin fibers, comprising applying at least one azodye of the general formula (I) to the keratin fibers:

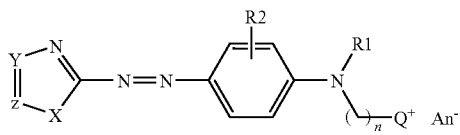

(I)

wherein
X is selected from the group consisting of oxygen, sulfur, N—R3 and C—R4;
Y is selected from the group consisting of C—R5, nitrogen, N—R6, sulfur and oxygen;
Z is C—R7 or nitrogen;
with the proviso that the heterocycle of the formula (I) comprises at least two and at most three heteroatoms, where the heterocycle has at most one sulfur atom or one oxygen atom;
n is an integer from 1 to 6;
R1 is selected from the group consisting of hydrogen, a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;
R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;
or if Y and Z are C—R5 and C—R7, the radical groups R5 and R7, together with the remaining molecule, can form a heterocyclic or carbocyclic, saturated or unsaturated, substituted or unsubstituted ring system;
or if X and Y are C—R4 and C—R5, the radical groups R4 and R5, together with the remaining molecule, can form a heterocyclic or carbocyclic, saturated or unsaturated, substituted or unsubstituted ring system;
R3 and R6 may be identical or different and, independently of one another, are selected from the group consisting of a saturated or unsaturated ($C_1$-$C_{12}$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group and a substituted or unsubstituted benzyl group;
Q+ represents an aromatic or non aromatic, substituted or unsubstituted 4- to 6-membered heterocyclic quaternary ammonium group, which may contain other heteroatoms selected from the group consisting of nitrogen, sulfur and oxygen, with the proviso that the cationic heterocycle comprises at most three heteroatoms, where the heterocycle has at most one sulfur atom or oxygen atom;
or the radical group R1, together with Q+, can form a 5 or 6-membered unsaturated heterocyclic, substituted or unsubstituted cationic ring system;
the anion An- is an organic or inorganic acid anion.

3. An agent for the simultaneous lightening and coloring of keratin fibers, comprising at least one oxidizing agent and at least one azodye of the general formula (I);

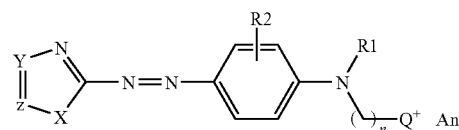

(I)

wherein
X is selected from the group consisting of oxygen, sulfur, N—R3 and C—R4;
Y is selected from the group consisting of C—R5, nitrogen, N—R6, sulfur and oxygen;
Z is C—R7 or nitrogen;
with the proviso that the heterocycle of the formula (I) comprises at least two and at most three heteroatoms, where the heterocycle has at most one sulfur atom or one oxygen atom;
n is an integer from 1 to 6;
R1 is selected from the group consisting of hydrogen, a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;
R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;
or if Y and Z are C—R5 and C—R7, the radical groups R5 and R7, together with the remaining molecule, can form a heterocyclic or carbocyclic, saturated or unsaturated, substituted or unsubstituted ring system;
or if X and Y are C—R4 and C—R5, the radical groups R4 and R5, together with the remaining molecule, can form a heterocyclic or carbocyclic, saturated or unsaturated, substituted or unsubstituted ring system;
R3 and R6 may be identical or different and, independently of one another, are selected from the group consisting of a saturated or unsaturated ($C_1$-$C_2$)-alkyl group, a ($C_1$-$C_{12}$)-alkyl group substituted by a halogen atom (F, Cl, Br, I), a hydroxy-($C_2$-$C_{12}$)-alkyl group, an amino-($C_1$-$C_2$)-alkyl group, a substituted or unsubstituted phenyl group and a substituted or unsubstituted benzyl group;
Q+ represents a 5- to 6-membered aromatic or non-aromatic heterocyclic quaternary ammonium group according to one formulas (IIa) to (IIg):

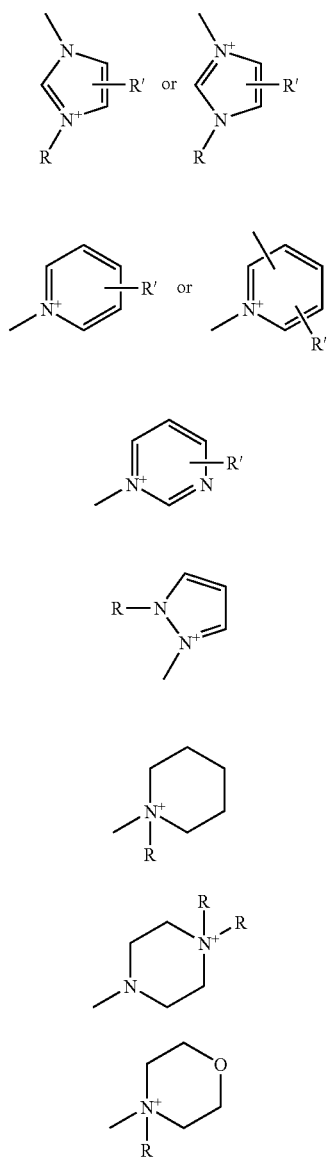

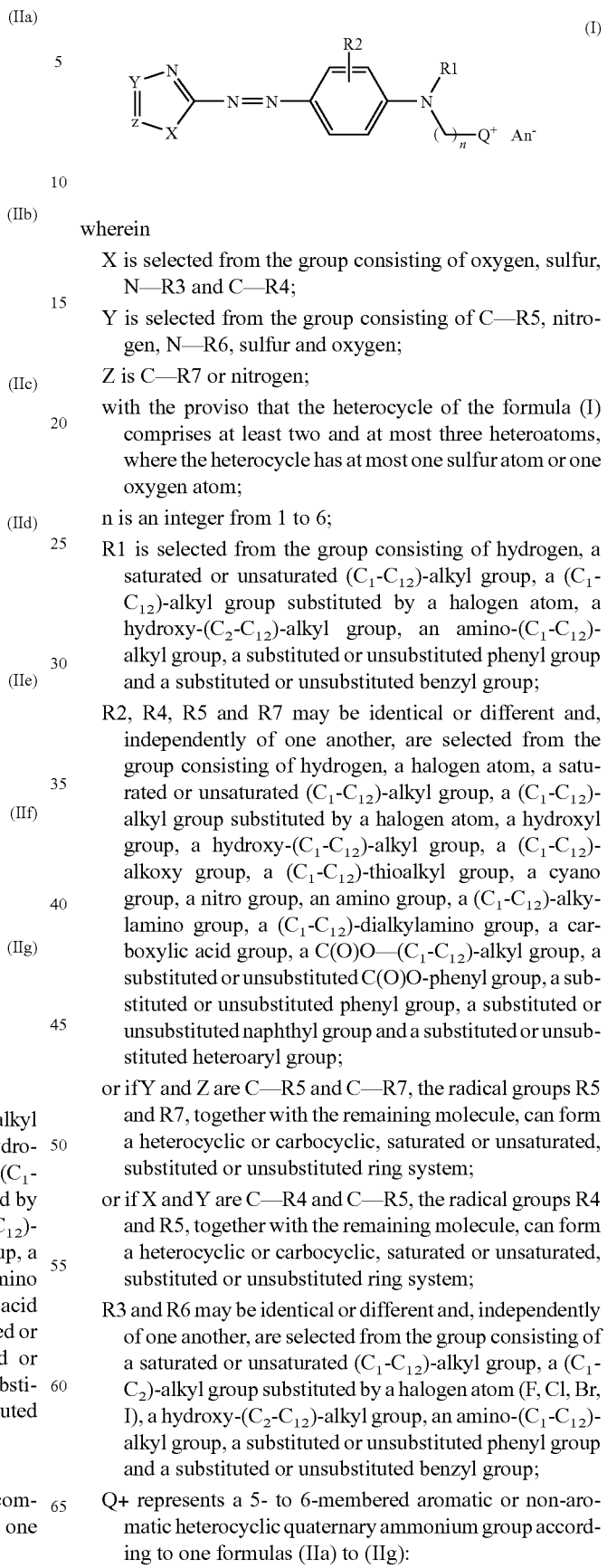

in which R is a saturated or unsaturated ($C_1$-$C_{12}$)-alkyl group, R' is selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;

the anion An- is an organic or inorganic acid anion.

4. An agent for oxidative coloring of keratin fibers comprising at least one oxidation dye precursor and at least one azodye of the general formula (I);

wherein

X is selected from the group consisting of oxygen, sulfur, N—R3 and C—R4;

Y is selected from the group consisting of C—R5, nitrogen, N—R6, sulfur and oxygen;

Z is C—R7 or nitrogen;

with the proviso that the heterocycle of the formula (I) comprises at least two and at most three heteroatoms, where the heterocycle has at most one sulfur atom or one oxygen atom;

n is an integer from 1 to 6;

R1 is selected from the group consisting of hydrogen, a saturated or unsaturated ($C_1$-$C_{12}$)-alkyl group, a ($C_1$-$C_{12}$)-alkyl group substituted by a halogen atom, a hydroxy-($C_2$-$C_{12}$)-alkyl group, an amino-($C_1$-$C_{12}$)-alkyl group, a substituted or unsubstituted phenyl group and a substituted or unsubstituted benzyl group;

R2, R4, R5 and R7 may be identical or different and, independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a ($C_1$-$C_{12}$)-thioalkyl group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group;

or if Y and Z are C—R5 and C—R7, the radical groups R5 and R7, together with the remaining molecule, can form a heterocyclic or carbocyclic, saturated or unsaturated, substituted or unsubstituted ring system;

or if X and Y are C—R4 and C—R5, the radical groups R4 and R5, together with the remaining molecule, can form a heterocyclic or carbocyclic, saturated or unsaturated, substituted or unsubstituted ring system;

R3 and R6 may be identical or different and, independently of one another, are selected from the group consisting of a saturated or unsaturated ($C_1$-$C_{12}$)-alkyl group, a ($C_1$-$C_2$)-alkyl group substituted by a halogen atom (F, Cl, Br, I), a hydroxy-($C_2$-$C_{12}$)-alkyl group, an amino-($C_1$-$C_{12}$)-alkyl group, a substituted or unsubstituted phenyl group and a substituted or unsubstituted benzyl group;

Q+ represents a 5- to 6-membered aromatic or non-aromatic heterocyclic quaternary ammonium group according to one formulas (IIa) to (IIg):

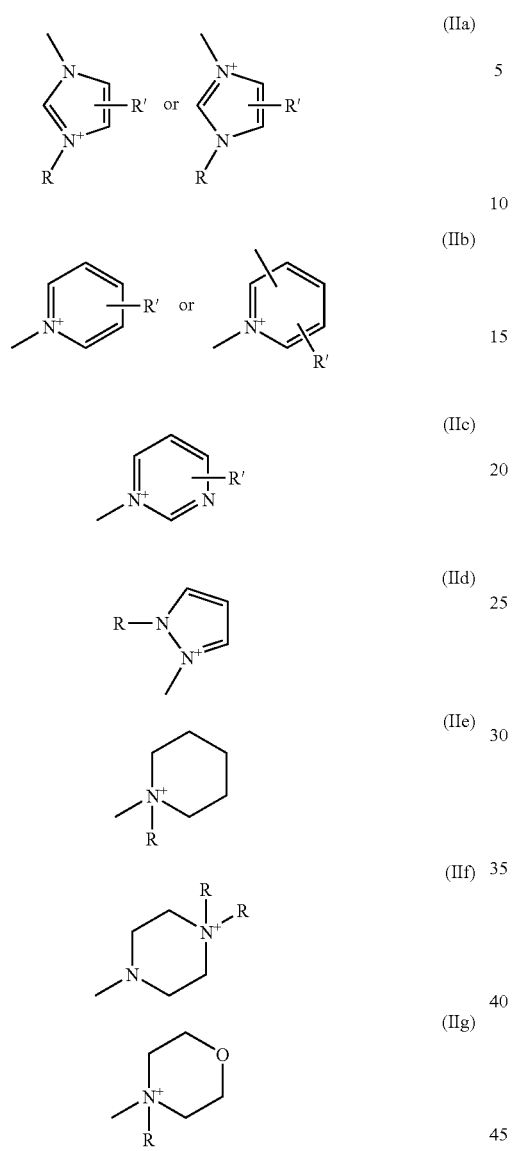

in which R is a saturated or unsaturated $(C_1-C_{12})$-alkyl group, R' is selected from the group consisting of hydrogen, a halogen atom, a saturated or unsaturated $(C_1-C_{12})$-alkyl group, a $(C_1-C_{12})$-alkyl group substituted by a halogen atom, a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a $C(O)O$—$(C_1-C_{12})$-alkyl group, a substituted or unsubstituted C(O)O-phenyl group, a substituted or unsubstituted phenyl group, a substituted or unsubstituted naphthyl group and a substituted or unsubstituted heteroaryl group;

the anion An- is an organic or inorganic acid anion.

5. A composition according to claim 1, wherein in said formula (I) Q+ represents a 5- to 6-membered aromatic or non-aromatic heterocyclic quaternary ammonium group according to one formulas (IIa) to (IIg)

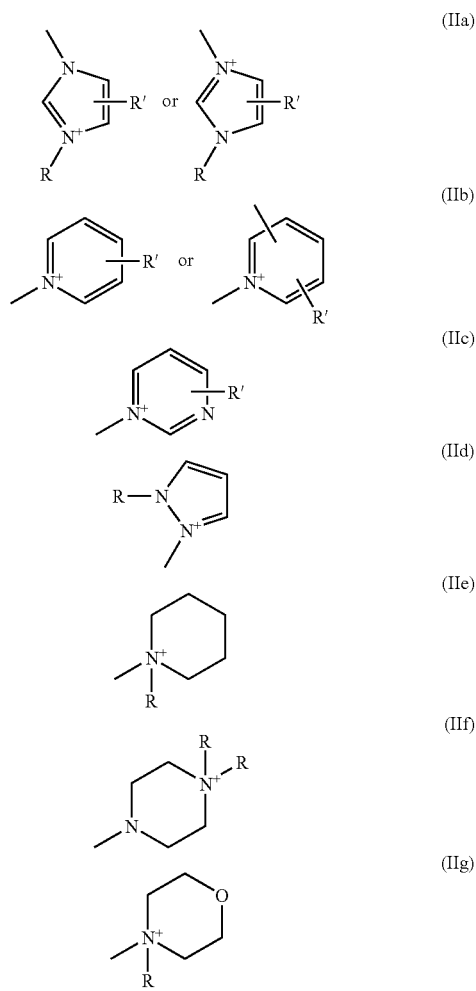

in which R is a saturated or unsaturated $(C_1-C_{12})$-alkyl group, R' is selected from the group consisting of hydrogen, a halogen atom, a saturated or unsaturated $(C_1-C_{12})$-alkyl group, a $(C_1-C_{12})$-alkyl group substituted by a halogen atom, a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a $C(O)O$—$(C_1-C_{12})$-alkyl group, a substituted or unsubstituted C(O)O-phenyl group, a substituted or unsubstituted phenyl group, a substituted or unsubstituted naphthyl group and a substituted or unsubstituted heteroaryl group.

6. A method according to claim 2, wherein in said formula (I) Q+ represents a 5- to 6-membered aromatic or non-aromatic heterocyclic quaternary ammonium group according to one formulas (IIa) to (IIg)

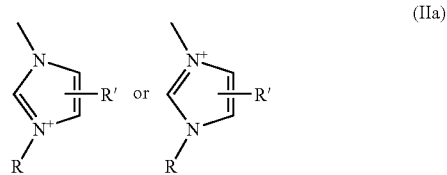

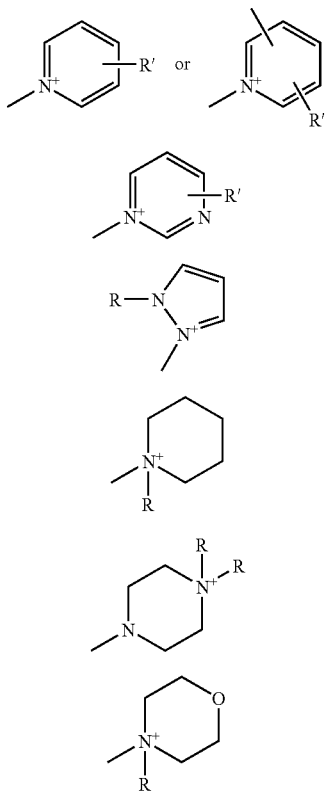

in which R is a saturated or unsaturated ($C_1$-$C_{12}$)-alkyl group, R' is selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, a substituted or unsubstituted naphthyl group and a substituted or unsubstituted heteroaryl group.

7. A composition according to claim 1, wherein said cationic azodye of said formula (I) is selected from the group consisting of 1-[2-(ethyl {4-[1,3-thiazol-2-yldiazenyl]phenyl}amino)ethyl]-3-methyl-1H-imidazol-3-ium bromide; 3-methyl-1-[2-(methyl{4-[1,3-thiazol-2-yldiazenyl]phenyl}amino)ethyl]-1H-imidazol-3-ium bromide; 1-[2-((2-hydroxyethyl) {4-[1,3-thiazol-2-yldiazenyl]phenyl}amino)ethyl]-3-methyl-1H-imidazol-3-ium bromide; 1-[2-(ethyl{3-methyl-4-[1,3-thiazol-2-yldiazenyl]phenyl}amino)ethyl]-3-methyl-1H-imidazol-3-ium bromide; 1-{2-[{3-chloro-4-[1,3-thiazol-2-yldiazenyl]phenyl}(ethyl)amino]ethyl}-3-methyl-1H-imidazol-3-ium bromide; 1-[2-(ethyl{4-[(4-methyl-1,3-thiazol-2-yl)diazenyl]phenyl}amino)ethyl]-3-methyl-1H-imidazol-3-ium bromide; 1-[2-(ethyl{3-methyl-4-[(4-methyl-1,3-thiazol-2-yl)diazenyl]phenyl}amino)-ethyl]-3-methyl-1H-imidazol-3-ium bromide; 1-{2-[{3-chloro-4-[(4-methyl-1,3-thiazol-2-yl)diazenyl]phenyl}(ethyl)amino]ethyl}-3-methyl-1H-imidazol-3-ium bromide; 1-[2-(ethyl{4-[(5-methyl-1,3-thiazol-2-yl)diazenyl]-phenyl}amino)ethyl]-3-methyl-1H-imidazol-3-ium bromide; 1-[2-(ethyl{3-methyl-4-[(5-methyl-1,3-thiazol-2-yl)diazenyl]phenyl}amino)ethyl]-3-methyl-1H-imidazol-3-ium bromide; 1-{2-[{3-chloro-4-[(5-methyl-1,3-thiazol-2-yl)diazenyl]phenyl}(ethyl)amino]ethyl}-3-methyl-1H-imidazol-3-ium bromide; 1-{2-[{4-[(4,5-dimethyl-1,3-thiazol-2-yl)diazenyl]-phenyl}(ethyl)amino]ethyl}-3-methyl-1H-imidazol-3-ium bromide; 1-{2-[{4-[(4,5-dimethyl-1,3-thiazol-2-yl)diazenyl]-3-methylphenyl}(ethyl)-amino]ethyl}-3-methyl-1H-imidazol-3-ium bromide; 1-{2-[{3-chloro-4-[(4,5-dimethyl-1,3-thiazol-2-yl)diazenyl]phenyl}(ethyl)amino]ethyl}-3-methyl-1H-imidazol-3-ium bromide; 1-[2-(ethyl{4-[(5-nitro-1,3-thiazol-2-yl)diazenyl]phenyl}amino)ethyl]-3-methyl-1H-imidazol-3-ium bromide; 1-{2-[{4-[(4-chloro-5-nitro-1,3-thiazol-2-yl)diazenyl]phenyl}(ethyl)-amino]ethyl}-3-methyl-1H-imidazol-3-ium bromide; 1-[2-(ethyl{4-[(4-phenyl-1,3-thiazol-2-yl)diazenyl]phenyl}amino)ethyl]-3-methyl-1H-imidazol-3-ium bromide;

1-{2-[{4-[1,3-benzothiazol-2-yldiazenyl]-phenyl}(ethyl)amino]ethyl}-3-methyl-1H-imidazol-3-ium bromide; 1-[2-(ethyl{4-[(6-nitro-1,3-benzothiazol-2-yl)diazenyl]phenyl}amino)ethyl]-3-methyl-1H-imidazol-3-ium bromide; 1-[2-(ethyl{4-[(4,6-dinitro-1,3-benzothiazol-2-yl)diazenyl]phenyl}amino)ethyl]-3-methyl-1H-imidazol-3-ium bromide; 1-[2-(ethyl{4-[(5,6-dinitro-1,3-benzothiazol-2-yl)diazenyl]-phenyl}amino)ethyl]-3-methyl-1H-imidazol-3-ium bromide; 1-[2-(ethyl{4-[1H-[1,3]thiazolo[5,4-f]indazol-6-yldiazenyl]phenyl}amino)ethyl]-3-methyl-1H-imidazol-3-ium bromide; 1-{2-[{4-[(5-chloro[1,3]thiazolo[5,4-b]pyridin-2-yl)diazenyl]phenyl}(ethyl)amino]ethyl}-3-methyl-1H-imidazol-3-ium bromide; 1-{2-[ethyl(4-{[5-(methoxy)[1,3]thiazolo[5,4-b]pyridin-2-yl]diazenyl}phenyl)amino]ethyl}-3-methyl-1H-imidazol-3-ium bromide;

1-[2-(ethyl{4-[1,3-thiazol-2-yldiazenyl]phenyl}amino)ethyl]-2,3-dimethyl-1H-imidazol-3-ium bromide; 1-[2-(ethyl{4-[(4-methyl-1,3-thiazol-2-yl)diazenyl]phenyl}amino)ethyl]-2,3-dimethyl-1H-imidazol-3-ium bromide; 1-[2-(ethyl{4-[(5-methyl-1,3-thiazol-2-yl)diazenyl]phenyl}amino)ethyl]-2,3-dimethyl-1H-imidazol-3-ium bromide; 1-{2-[{4-[(4,5-dimethyl-1,3-thiazol-2-yl)diazenyl]phenyl}(ethyl)amino]ethyl}-2,3-dimethyl-1H-imidazol-3-ium bromide; 1-[3-(ethyl{4-[1,3-thiazol-2-yldiazenyl]phenyl}amino)propyl]-3-methyl-1H-imidazol-3-ium bromide; 1-[2-(ethyl{4-[1,3-thiazol-2-yldiazenyl]phenyl}amino)ethyl]-pyridinium bromide; 1-[2-(ethyl{4-[(5-methyl-1,3-thiazol-2-yl)diazenyl]-phenyl}amino)ethyl]pyridinium bromide; 1-[2-(ethyl{4-[(4-methyl-1,3-thiazol-2-yl)diazenyl]phenyl}amino)ethyl]-pyridinium bromide; 1-{2-[{4-[(4,5-dimethyl-1,3-thiazol-2-yl)diazenyl]-phenyl}(ethyl)amino]-ethyl}pyridinium bromide; 1-[2-(ethyl{3-methyl-4-[1,3-thiazol-2-yldiazenyl]-phenyl}amino)ethyl]pyridinium bromide; 1-{2-[{3-chloro-4-[1,3-thiazol-2-yldiazenyl]phenyl}(ethyl)amino]ethyl}pyridinium bromide; 1-[2-(ethyl{4-[(5-nitro-1,3-thiazol-2-yl)diazenyl]phenyl}amino)ethyl]pyridinium bromide; 1-[2-(ethyl{3-methyl-4-[(5-nitro-1,3-thiazol-2-yl)diazenyl]phenyl}amino)-ethyl]pyridinium bromide;

1-{2-[{3-(dimethylamino)-4-[1,3-thiazol-2-yldiazenyl]phenyl}(ethyl)amino]ethyl}-pyridinium bromide; 1-{2-[{3-(dimethylamino)-4-[(5-nitro-1,3-thiazol-2-yl)diazenyl]-phenyl}(ethyl)amino]ethyl}pyridinium bromide; 4-[2-(ethyl{4-[1,3-thiazol-2-yldiazenyl]phenyl}amino)

ethyl]-4-methylmorpholin-4-ium bromide; 4-{2-[{4-[1,3-benzothiazol-2-yldiazenyl]phenyl}(ethyl)amino]ethyl}-4-methylmorpholin-4-ium bromide; 1-[2-(ethyl{4-[1,3-thiazol-2-yldiazenyl]-phenyl}amino)ethyl]-1-methylpiperidinium bromide; 4-[2-(ethyl{4-[1,3-thiazol-2-yldiazenyl]phenyl}amino)ethyl]-1,1-dimethylpiperazin-1-ium bromide; 1-[2-(ethyl{4-[1,3,4-thiadiazol-2-yldiazenyl]phenyl}amino)ethyl]-3-methyl-1H-imidazol-3-ium bromide; 1-[2-(ethyl{4-[(5-phenyl-1,3,4-thiadiazol-2-yl)diazenyl]phenyl}amino)ethyl]-3-methyl-1H-imidazol-3-ium bromide; 1-[2-(ethyl{4-[1,3,4-thiadiazol-2-yldiazenyl]phenyl}amino)-ethyl]pyridinium bromide; 1-[2-(ethyl{4-[(5-phenyl -1,3,4-thiadiazol-2-yl)diazenyl]phenyl}amino)ethyl]-pyridinium bromide; 1-[2-(ethyl{4-[1,2,4-thiadiazol-2-yldiazenyl]phenyl}amino)ethyl]-3-methyl-1H-imidazol-3-ium bromide; 1-[2-(ethyl{4-[(3-phenyl-1,2,4-thiadiazol-5-yl)diazenyl]-phenyl}amino)ethyl]-3-methyl-1H-imidazol-3-ium bromide; 1-{2-[{4-[(3-chloro-1,2,4-thiadiazol-5-yl)diazenyl]-phenyl}(ethyl)amino]-ethyl}-3-methyl -1H-imidazol-3-ium bromide; 1-[2-(ethyl{4-[1,2,4-thiadiazol-5-yldiazenyl]phenyl}amino)ethyl]pyridinium bromide; 1-[2-(ethyl{4-[(3-phenyl-1,2,4-thiadiazol-5-yl)diazenyl]phenyl}amino)ethyl]-pyridinium bromide; 2-(ethyl{4-[1H-1,2,4-triazol-5-yldiazenyl]-phenyl}amino)-3-methyl-1H-imidazol-3-ium bromide; 1-[2-(ethyl{4-[(1-methyl-1H-imidazol-2-yl)diazenyl]-phenyl}amino)ethyl]-3-methyl-1H-imidazol-3-ium bromide; 1-[2-(ethyl{3-methyl-4-[(1-methyl-1H-imidazol-2-yl)diazenyl]phenyl}amino)ethyl]-3-methyl-1H-imidazol-3-ium bromide and 1-{2-[{3-chloro-4-[(1-methyl-1H-imidazol-2-yl)diazenyl]phenyl}-(ethyl)amino]ethyl}-3-methyl-1H -imidazol-3-ium bromide.

8. A method according to claim 2, wherein said cationic azodye of said formula (I) is selected from the group consisting of 1-[2-(ethyl{4-[1,3-thiazol-2-yldiazenyl]phenyl}amino)ethyl]-3-methyl-1H-imidazol-3-ium bromide; 3-methyl-1-[2-(methyl{4-[1,3-thiazol-2-yldiazenyl]phenyl}amino)ethyl]-1H-imidazol-3-ium bromide; 1-[2-((2-hydroxyethyl) {4-[1,3-thiazol-2-yldiazenyl]phenyl}amino)ethyl]-3-methyl-1H-imidazol-3-ium bromide; 1-[2-(ethyl{3-methyl-4-[1,3-thiazol-2-yldiazenyl]phenyl}amino)ethyl]-3-methyl-1H-imidazol-3-ium bromide; 1-{2-[{3-chloro-4-[1,3-thiazol-2-yldiazenyl]phenyl}(ethyl)amino]ethyl}-3-methyl-1H-imidazol-3-ium bromide; 1-[2-(ethyl{4-[(4-methyl-1,3-thiazol-2-yl)diazenyl]phenyl}amino)ethyl]-3-methyl-1H-imidazol-3-ium bromide; 1-[2-(ethyl{3-methyl-4-[(4-methyl-1,3-thiazol-2-yl)diazenyl]phenyl}amino)-ethyl]-3-methyl-1H-imidazol-3-ium bromide; 1-{2-[{3-chloro-4-[(4-methyl-1,3-thiazol-2-yl)diazenyl]phenyl}(ethyl)amino]ethyl}-3-methyl-1H-imidazol-3-ium bromide; 1-[2-(ethyl{4-[(5-methyl-1,3-thiazol-2-yl)diazenyl]-phenyl}amino)ethyl]-3-methyl-1H-imidazol-3-ium bromide; 1-[2-(ethyl{3-methyl-4-[(5-methyl-1,3-thiazol-2-yl)diazenyl]phenyl}amino)ethyl]-3-methyl-1H-imidazol-3-ium bromide; 1-{2-[{3-chloro-4-[(5-methyl-1,3-thiazol-2-yl)diazenyl]phenyl}(ethyl)amino]ethyl}-3-methyl-1H-imidazol-3-ium bromide; 1-{2-[{4-[(4,5-dimethyl-1,3-thiazol-2-yl)diazenyl]-phenyl}(ethyl)amino]ethyl}-3-methyl-1H-imidazol-3-ium bromide; 1-{2-[{4-[(4,5-dimethyl-1,3-thiazol-2-yl)diazenyl]-3-methylphenyl}(ethyl)-amino]ethyl}-3-methyl-1H-imidazol-3-ium bromide; 1-{2-[{3-chloro-4-[(4,5-dimethyl-1,3-thiazol-2-yl)diazenyl]phenyl}(ethyl)amino]ethyl}-3-methyl-1H-imidazol-3-ium bromide; 1-[2-(ethyl{4-[(5-nitro-1,3-thiazol-2-yl)diazenyl]phenyl}amino)ethyl]-3-methyl-1H-imidazol-3-ium bromide; 1-{2-[{4-[(4-chloro-5-nitro-1,3-thiazol-2-yl)diazenyl]phenyl}(ethyl)-amino]ethyl}-3-methyl-1H-imidazol-3-ium bromide; 1-[2-(ethyl{4-[(4-phenyl-1,3-thiazol-2-yl)diazenyl]phenyl}amino)ethyl]-3-methyl-1H-imidazol-3-ium bromide;

1-{2-[{4-[1,3-benzothiazol-2-yldiazenyl]-phenyl}(ethyl)amino]ethyl}-3-methyl-1H-imidazol-3-ium bromide; 1-[2-(ethyl{4-[(6-nitro-1,3-benzothiazol-2-yl)diazenyl]phenyl}amino)ethyl]-3-methyl-1H-imidazol-3-ium bromide; 1-[2-(ethyl {4-[(4,6-dinitro-1,3-benzothiazol-2-yl)diazenyl]phenyl}amino)ethyl]-3-methyl-1H-imidazol-3-ium bromide; 1-[2-(ethyl{4-[(5,6-dinitro-1,3-benzothiazol-2-yl)diazenyl]-phenyl}amino)ethyl]-3-methyl-1H-imidazol-3-ium bromide; 1-[2-(ethyl{4-[1H-[1,3]thiazolo[5,4-f]indazol-6-yldiazenyl]phenyl}amino)ethyl]-3-methyl-1H-imidazol-3-ium bromide; 1-{2-[{4-[(5-chloro[1,3]thiazolo[5,4-b]pyridin-2-yl)diazenyl]phenyl}(ethyl)amino]ethyl}-3-methyl-1H-imidazol-3-ium bromide; 1-{2-[ethyl(4-{[5-(methoxy)[1,3]thiazolo[5,4-b]pyridin-2-yl]diazenyl}phenyl)amino]ethyl}-3-methyl-1H-imidazol-3-ium bromide;

1-[2-(ethyl{4-[1,3-thiazol-2-yldiazenyl]phenyl}amino)ethyl]-2,3-dimethyl-1H-imidazol-3-ium bromide; 1-[2-(ethyl{4-[(4-methyl-1,3-thiazol-2-yl)diazenyl]phenyl}amino)ethyl]-2,3-dimethyl-1H-imidazol-3-ium bromide; 1-[2-(ethyl{4-[(5-methyl-1,3-thiazol-2-yl)diazenyl]phenyl}amino)ethyl]-2,3-dimethyl-1H-imidazol-3-ium bromide; 1-{2-[{4-[(4,5-dimethyl-1,3-thiazol-2-yl)diazenyl]phenyl}(ethyl)amino]ethyl}-2,3-dimethyl-1H-imidazol-3-ium bromide; 1-[3-(ethyl{4-[1,3-thiazol-2-yldiazenyl]phenyl}amino)propyl]-3-methyl-1H-imidazol-3-ium bromide; 1-[2-(ethyl{4-[1,3-thiazol-2-yldiazenyl]phenyl}amino)ethyl]-pyridinium bromide; 1-[2-(ethyl{4-[(5-methyl-1,3-thiazol-2-yl)diazenyl]-phenyl}amino)ethyl]pyridinium bromide; 1-[2-(ethyl{4-[(4-methyl-1,3-thiazol-2-yl)diazenyl]phenyl}amino)ethyl]-pyridinium bromide; 1-{2-[{4-[(4,5-dimethyl-1,3-thiazol-2-yl)diazenyl]-phenyl}(ethyl)amino]-ethyl}pyridinium bromide; 1-[2-(ethyl{3-methyl-4-[1,3-thiazol-2-yldiazenyl]-phenyl}amino)ethyl]pyridinium bromide; 1-{2-[{3-chloro-4-[1,3-thiazol-2-yldiazenyl]phenyl}(ethyl)amino]ethyl}pyridinium bromide; 1-[2-(ethyl{4-[(5-nitro-1,3-thiazol-2-yl)diazenyl]phenyl}amino)ethyl]pyridinium bromide; 1-[2-(ethyl{3-methyl-4-[(5-nitro-1,3-thiazol-2-yl)diazenyl]phenyl}amino)-ethyl]pyridinium bromide;

1-{2-[{3-(dimethylamino)-4-[1,3-thiazol-2-yldiazenyl]phenyl}(ethyl)amino]ethyl}-pyridinium bromide; 1-{2-[{3-(dimethylamino)-4-[(5-nitro-1,3-thiazol-2-yl)diazenyl]-phenyl}(ethyl)amino]ethyl}pyridinium bromide; 4-[2-(ethyl{4-[1,3-thiazol-2-yldiazenyl]phenyl}amino)ethyl]-4-methylmorpholin-4-ium bromide; 4-{2-[{4-[1,3-benzothiazol-2-yldiazenyl]phenyl}(ethyl)amino]ethyl}-4-methylmorpholin-4-ium bromide; 1-[2-(ethyl{4-[1,3-thiazol-2-yldiazenyl]-phenyl}amino)ethyl]-1-methylpiperidinium bromide; 4-[2-(ethyl{4-[1,3-thiazol-2-yldiazenyl]phenyl}amino)ethyl]-1,1-dimethylpiperazin-1-ium bromide; 1-[2-(ethyl{4-[1,3,4-thiadiazol-2-yldiazenyl]phenyl}amino)ethyl]-3-methyl-1H-imidazol-3-ium bromide; 1-[2-(ethyl{4-[(5-phenyl-1,3,4-thiadiazol-2-yl)diazenyl]phenyl}amino)ethyl]-3-methyl-1H-imidazol-3-ium bromide; 1-[2-(ethyl{4-[1,3,4-thiadiazol-2-yldiazenyl]phenyl}amino)-ethyl]pyridinium bromide; 1-[2-

(ethyl{4-[(5-phenyl-1,3,4-thiadiazol-2-yl)diazenyl]phenyl}amino)ethyl]-pyridinium bromide; 1-[2-(ethyl{4-[1,2,4-thiadiazol-2-yldiazenyl]phenyl}amino)ethyl]-3-methyl-1H-imidazol-3-ium bromide; 1-[2-(ethyl{4-[(3-phenyl-1,2,4-thiadiazol-5-yl)diazenyl]-phenyl}amino)ethyl]-3-methyl-1H-imidazol-3-ium bromide; 1-{2-[{4-[(3-chloro-1,2,4-thiadiazol-5-yl)diazenyl]-phenyl}(ethyl)amino]-ethyl}-3-methyl-1H-imidazol-3-ium bromide; 1-[2-(ethyl{4-[1,2,4-thiadiazol-5-yldiazenyl]phenyl}amino)ethyl]pyridinium bromide; 1-[2-(ethyl{4-[(3-phenyl-1,2,4-thiadiazol-5-yl)diazenyl]phenyl}amino)ethyl]-pyridinium bromide; 2-(ethyl{4-[1H-1,2,4-triazol-5-yldiazenyl]-phenyl}amino)-3-methyl-1H-imidazol-3-ium bromide; 1-[2-(ethyl{4-[(1-methyl-1H-imidazol-2-yl)diazenyl]-phenyl}amino)ethyl]-3-methyl -1H-imidazol-3-ium bromide; 1-[2-(ethyl{3-methyl-4-[(1-methyl-1H-imidazol-2-yl)diazenyl]phenyl}amino)ethyl]-3-methyl-1H-imidazol-3-ium bromide and 1-{2-[{3-chloro-4-[(1-methyl-1H-imidazol-2-yl)diazenyl]phenyl}-(ethyl)amino]ethyl}-3-methyl-1H-imidazol-3-ium bromide.

9. A composition according to claim 1, wherein the agent comprises from 0.01 to 10% by weight of said cationic azodye of said formula (I).

10. A composition according to claim 1, wherein said composition is a hair colorant composition.

* * * * *